United States Patent [19]

Lynnworth

[11] Patent Number: 5,515,733

[45] Date of Patent: May 14, 1996

[54] ULTRASONIC TRANSDUCER SYSTEM WITH CROSSTALK ISOLATION

[75] Inventor: Lawrence C. Lynnworth, Waltham, Mass.

[73] Assignee: Panametrics, Inc., Waltham, Mass.

[21] Appl. No.: 176,930

[22] Filed: Jan. 3, 1994

Related U.S. Application Data

[63] Continuation-in-part of Ser. No. 670,702, Mar. 18, 1991, Pat. No. 5,275,060.

[51] Int. Cl.$^6$ ........................................... G02F 1/66
[52] U.S. Cl. ........................................... 73/861.27; 73/644
[58] Field of Search ........................... 73/861.26, 861.27, 73/861.28, 861.29, 861.31, 19.03, 644, 24.06, 31.05, 54.41, 61.45, 61.49, 61.79, 64.53

[56] References Cited

U.S. PATENT DOCUMENTS

| | | | |
|---|---|---|---|
| 3,771,117 | 11/1973 | Shaffer et al. | 73/861.27 X |
| 3,921,442 | 11/1975 | Soloway | 73/644 |
| 4,417,480 | 11/1983 | Zacharias, Jr. | 73/861.27 X |
| 4,532,812 | 8/1985 | Birchak | 73/861.27 |
| 4,536,673 | 8/1985 | Forster | 73/644 X |
| 4,596,133 | 6/1986 | Smalling et al. | 73/24 |
| 4,742,717 | 5/1988 | Ichino | 73/866.5 |
| 4,783,997 | 11/1988 | Lynnworth | 73/644 |
| 5,329,821 | 7/1994 | Birnbaum et al. | 73/861.27 X |

OTHER PUBLICATIONS

Bragg et al., "Internally–Nonprotruding One–Port Ultrasonic Flow Sensor for Air and Some Other Gases" *Fourth European Conference on CONTROL 94* at the University of Warwick, Conventry, UK, Paper no. 470, pp. 1–16, 21–24 Mar. 1994.

*Cajon Company*, "Vacuum Tubing Products" Catalog No. CA–787, 1988.

*Cajon Vacum Products*, Catalog No. CA–877A, "Stainless Steel Tubing with rubber hose flexibility" and "Ultra–Torr Fittings", pp. 8–9, No. 321.

Kaimal et al., "A Continuous Wave Sonic Anemometer––Thermometer" *Journal of Applied Meteorology*, vol. 2, No. 1, pp. 156–164 and 180–186, Feb. 1963.

Kou et al., "A Pulsed Phase Measurement Ultrasonic Flowmeter for Medical Gases" *Annals of Biomedical Engineering*, vol. 12, pp. 263–280, 1984.

Lynnworth et al., "Slow–Wave Acoustic Isolation for Measurement of Flow" *NASA Technical Briefs*, vol. 17, No. 11, pp. 77, Nov. 1993.

National O–Rings, Industrial Maintenance Guide, 915, pp. 1–13, (1985, 1988).

A. von Jena et al., "Ultrasound gas–flow meter for household application" *Sensors and Actuators A*, 37–38, pp. 135–140, 1993.

*Primary Examiner*—Richard Chilcot
*Assistant Examiner*—Elizabeth L. Dougherty
*Attorney, Agent, or Firm*—Lahive & Cockfield

[57] ABSTRACT

Transducers are mounted in a housing or vessel to propagate signals along a fluid measurement path, and a plurality of massive elements are placed between transmitting and receiving transducers in the acoustic propagation path through the solid body of the housing or vessel to remove crosstalk. In a preferred embodiment, the elements are rings, or sleeves which are attached to, or are machined from a thicker cylinder to leave a thin-walled cylinder with alternating masses. An isolation structure lightly sandwiches a flange between O-rings. This structure may be formed with flanged transducer casings, allowing the transducers to be closely spaced in solid conduits or on rigid frames without ringing. Alternatively, it may be formed in a separate framework or holder, providing precise positioning for interrogating gases in unconfined or loosely confined regions. Closed path sensor configurations measure circulation or swirl.

19 Claims, 20 Drawing Sheets

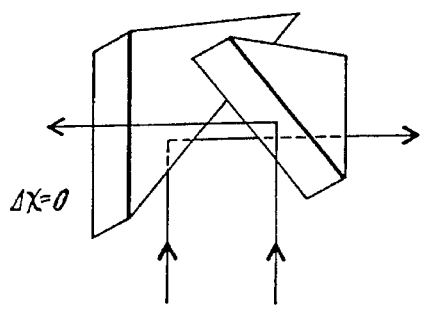
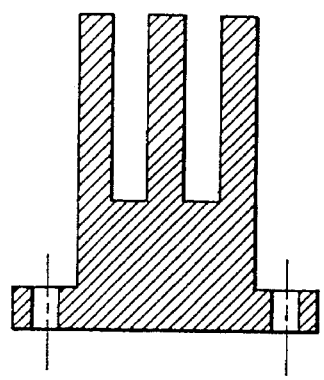
FIG. 20A  FIG. 20B
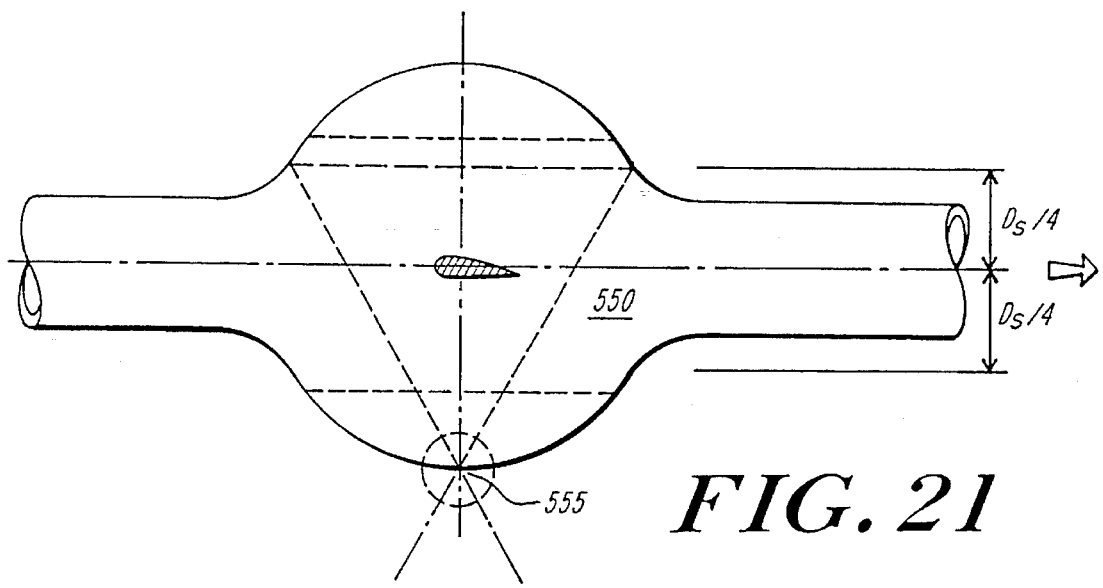
FIG. 21
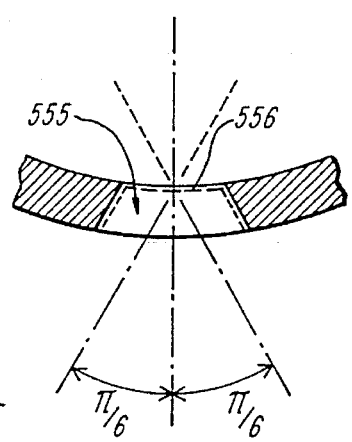
FIG. 21A

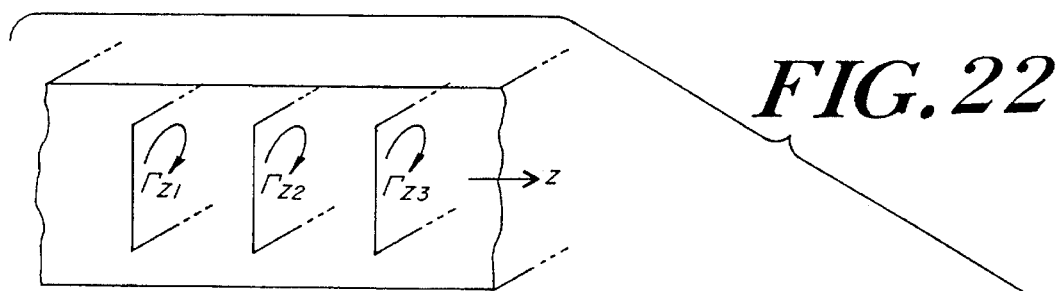
FIG.22
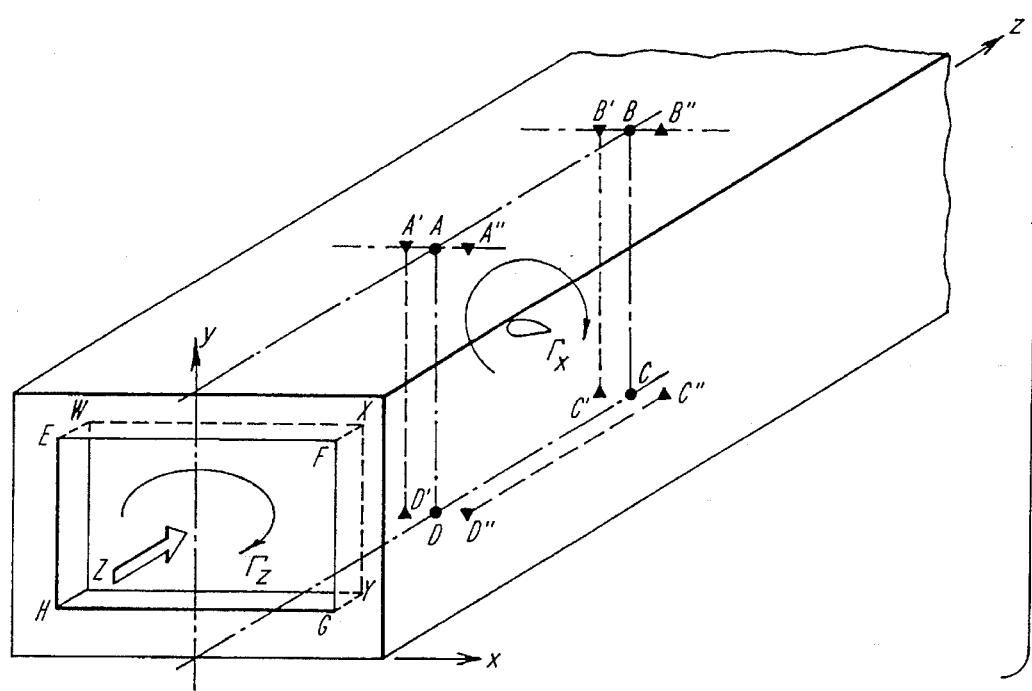
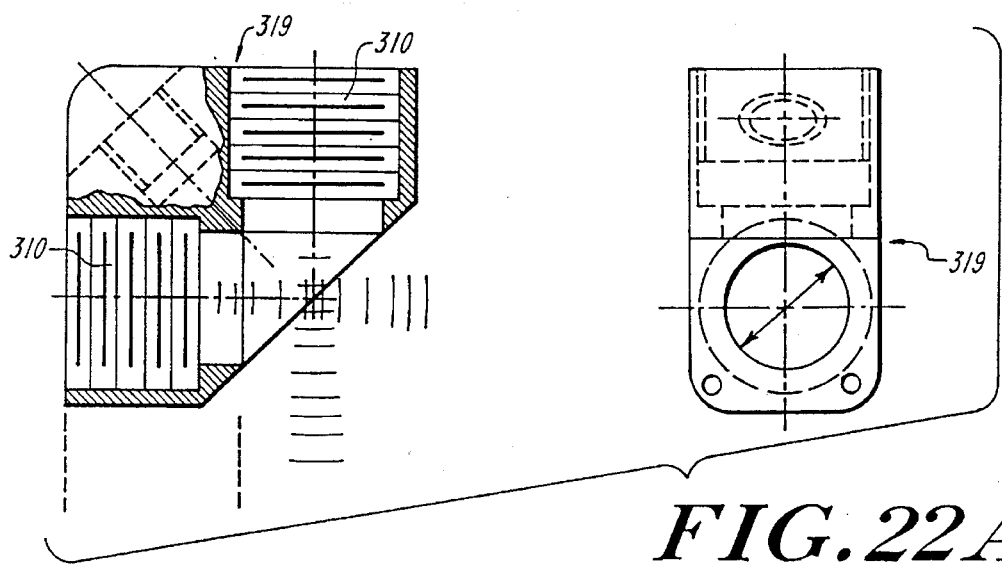
FIG.22A 5,515,733

1

ULTRASONIC TRANSDUCER SYSTEM WITH CROSSTALK ISOLATION

RELATED APPLICATIONS

This application is a continuation-in-part of U.S. Ser. No. 670,702, filed on Mar. 18, 1991. U.S. Pat. No. 5,275,060.

BACKGROUND OF THE INVENTION

The present invention relates to ultrasonic transducer and measurement systems of the type wherein an electrically actuated signal source, typically a piezoelectric crystal, is mounted in a mounting assembly fixed to a housing or wedge, or fixed directly to a conduit, to propagate ultrasonic signals through a medium flowing in the conduit. It particularly relates to such transducer and measurement systems wherein the medium has a low density, such as a gaseous medium, and wherein the size of the conduit or the signal path length through the medium raise considerations of crosstalk.

In these circumstances, the amount of signal energy which can be received through the medium is relatively small. Furthermore, because the signal propagates through the gas with a velocity different from and generally slower than its propagation velocity through the solid structure of the conduit, it can be difficult to find a suitable timing window in which the received signal can be dependably distinguished from ringing or other energy propagated directly through the conduit walls.

To some extent the problem of signal strength can be addressed by appropriate impedance matching and the use of a large-area diaphragm to couple the crystal to the medium. However, suitable isolation remains a problem, particularly in view of the relatively large amount of energy contained in the solid-path noise band.

One approach to this problem has been discussed in the inventor's previously filed U.S. patent application entitled Snap-On Flow Measurement System, filed on Jun. 29, 1990 as Ser. No. 546,586. In that application, specifically with reference to FIG. 15A thereof, a construction is shown involving acoustically massive rings or a spiral body interposed in the solid body acoustic path between the transmitting and receiving crystals. The present disclosure is directed to related constructions, further isolation structures, and different practical embodiments of such transducer isolation and mounting structures.

BRIEF DESCRIPTION OF THE INVENTION

In accordance with the present invention, a transducer is mounted in a housing or vessel to propagate signals along a gas interrogation path, and a plurality of isolation elements or mismatched impedance structures are placed between transmitting and receiving transducers in the noise propagation path through the solid body of the housing or vessel.

In one embodiment, the elements are massive rings, which are placed on a thin-walled cylindrical stand-off that supports the transducer on a conduit wall. Preferably the rings are closely spaced, or contiguous and contacting each other along at most a small point-like region, so that substantially all acoustic energy flows to or from each ring via the adjacent thin wall of the stand-off. In one embodiment, a thick-walled tube is machined to have plural radially oriented slots, yielding a structure of alternating masses. In a related embodiment, inner and outer thick-walled tubes are

2 each machined to form a sequence of thick rings separated by thin shells, and are joined at one end to provide a U-shaped mounting with a longer damping path in which the damping rings are enclosed in the interior of the re-entrant structure.

In another embodiment, a specially-configured O-ring mounting is interposed in the noise path to attenuate systemic noise. In different constructions utilizing this isolation structure, the transducer elements may themselves be secured by the O-rings, or the elements may be attached to structural members that are secured and isolated by O-rings. Particularly beneficial isolation properties are obtained by lightly sandwiching a mounting flange axially against or between rings, preferably rings formed of particular attenuating materials. In a further aspect of this embodiment, the fluid which is to be sensed may be contained or constrained in a thin walled vessel or conduit, such as a metal foil bellows, which does not itself possess sufficient dimensional stability for use as a flow cell, but which has a wall thickness selected so that signal propagation in the wall is slower than the signal's sound speed in the fluid. A separate holder or framework then supports the transducers and conduit. The bellows provides temporal isolation of the energy burst transmitted directly along the conduit, while the framework provides physical and dimensional rigidity, together with acoustic isolation by extended path, impedance mismatch, attenuating O-ring sandwich or a combination of these techniques.

Particular systems utilizing O-ring isolators may be compact, since the usual stand-offs, dampers and spatial isolators are not required. In particular, many transducers may be mounted on a single hole plug mount to perform multi-path, multi-range or multidirectional ultrasonic interrogation or reflectometry, or multiple transducers may be mounted on arms, lattices or countersunk holes aimed along different axes and effectively isolated from each other. Simple systems consisting of multiple plug-, flange- or frame-mounted transducers may operate in conduits or open regions to provide measurement devices such as a novel anemometer, a device to measure flow, lift or circulation about a structure in a wind tunnel, a system to measure swirl in a conduit, or a single-opening stack or duct gas density or flow meter.

These and other features of the invention will be understood from the description below, taken together with figures illustrating various embodiments thereof.

BRIEF DESCRIPTION OF THE DRAWINGS

FIGS. 18 and 18A illustrate a flange-mounted single-opening triple midradius path sensor;

FIGS. 20, 20A and 20B illustrate a wind tunnel circulation sensor;

FIGS. 21 and 21A illustrate a chordal circulation sensor in a contoured wind tunnel; and FIG. 22 illustrates closed path integration to measure aerodynamic quantities for an ultrasonic measurement of lift; and FIGS. 22A–22C illustrate different transducer mounts or measurement systems.

DETAILED DESCRIPTION

Figure 1:
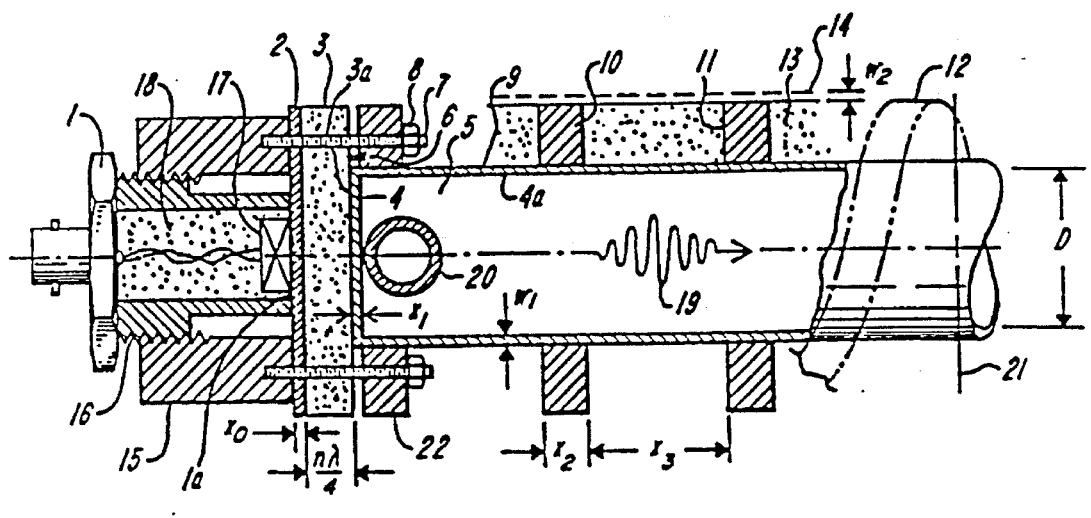
FIG. 1 shows a cross-sectional view of one ultrasonic transducer assembly.

FIG. 1 shows an ultrasonic transducer configuration as described in applicant's aforesaid U.S. patent application Ser. No. 546,586, the text of which is hereby incorporated by reference for a fuller description of the context and operation of the device. This embodiment has a transducer housing 1 which holds an electroacoustic signal generating element 17 to launch and receive ultrasonic signals indicated by 19.

The wave 19 exits from transducer housing 1 through the housing end window 1a, which may be made of plastic, ceramic or metal foil, via a relatively stiff plate 2 of thickness $x_o$. Plate 2 and housing end window 1a are illustrated as flat but may be slightly curved to simplify coupling or for other reasons. Plate 2, if used in the transducer construction, may be a stainless steel member with its thickness $x_o=0.05$ to 0.25 mm, for example. It is coupled or bonded to a quarter-wave impedance matcher 3 of thickness $n\lambda/4$, where n is an odd integer and $\lambda$ is the wavelength in the matcher. The wave 19 next passes through a cell end window 4, whose thickness $x_1$ is small compared to wavelength. For example, for a 100 kHz acoustic signal, where the compressional wavelength in stainless steel is about 50 mm, $x_1 \leq 0.1$ mm would be appropriate.

An end window this thin would deform if the cell were evacuated, unless the external atmospheric pressure were prevented from acting against the window, or unless the window were reinforced and stiffened. In FIG. 1 the window is stiffened by bonding the quarter-wave member to it, and also by sealing, as with an O-ring 6. Adapter 15 and plate 2 and matcher 3 are attached to an acoustically-massive ring 22 that is brazed, epoxied or otherwise bonded around the end region of the thin-wall tubular conduit 4a that comprises the major part of the cell 9. The attachment of this ring is accomplished by means of threaded studs 7 and nuts 8, or other conventional means. A gas entry port 20 is located near the inlet of cell 9, and another one, not shown, is symmetrically located near the other end of the symmetrical cell, symmetry being indicated by centerline 21. Gas 5 enters and exits through these ports, and its properties are measured by detection and correlation of acoustic signals passing therethrough.

The speed of sound in most gases is much slower than it is in typical engineering metals like stainless steel, and this may lead to an acoustic short circuit problem, as discussed in the applicant's book, Ultrasonic Measurements for Process Control, Academic press 1989, in chapters 3 and 4. However, if the thickness $w_1$ of wall 4a is sufficiently thin ($fw_1 \ll 1$ MHz.mm) then acoustic energy propagating as a lowest-order asymmetric ($A_o$)flexural wave will propagate at a phase velocity $c_f < c_{gas}$. In accordance with the present invention, energy propagating in the $A_o$ mode as well as in other modes is attenuated by introduction of a multiplicity of impedance mismatches along the conduit. Structures for this are illustrated in FIG. 1 and include acoustically-massive rings 10 and 11, or equivalently, internal thick sleeves (not shown) and an acoustically-massive spiral 12, any of which further serves as a mechanical reinforcement to support the thin conduit wall during evacuation or pressurization. In other embodiments, an internally contacting spiral or sleeves may intercept internal reflected energy and scatter it, thus removing spurious, unwanted (multi-path) gas-borne modes and sharpening the axially-transmitted gas-borne ultrasonic signal.

Further attenuation of the unwanted wall-born energy is accomplished in the embodiment of FIG. 1, by surrounding at least part of the conduit wall 4a with dampening material 13, Material 13 may be enclosed by another thin-wall tube 14 of thickness $w_2 \ll \lambda$. Soft elastomers such as silicone and fluorosilicone and some urethanes have been found to be effective absorbers for waves near 100 kHz or above. Such materials may also be used as a potting medium 18 within the transducer assembly 1. The spacing $x_3$ between rings 10 and 11, or between spiral turns, is preferably less than the pipe diameter D. The width $x_2$ of the massive rings is preferably on the order of one quarter wavelength of the wave to be blocked. If waves of several frequencies are to be blocked then the inter-ring spacing or dimension $x_2$ ought to be different for different rings; for the spiral embodiment, the pitch or thickness of successive turns of the spiral may vary.

The matcher 3 may be made of Emerson and Cumming syntactic foam, or for temperatures above the rating of such a plastic-based foam, of low-density or foamy grade of ceramic or graphite. In these examples, the matcher is stiff and capable of supporting pressure differentials. The matcher not only impedance matches but also serves to support the thin window 4. The outside surface of window 4 can also be "wrung" against matcher 3 using a thin layer of oil or other acoustic couplant along interface 3a. With such a coupling, the window 4 can be maintained flat, yet be removably coupled to the matcher. Plate 2, while thin, can be two to ten times thicker than the window 4 that faces the gas conduit, since plate 2 is on the high impedance part of the circuit, while the window 4 is on the low impedance side.

The housing of transducer assembly 1 may be metallic, e.g., aluminum, stainless steel or titanium, or may be plastic.

If plastic, it is preferably shielded electrically on the inside. The housing can also contain a first impedance matching layer (not shown) of impedance $Z_o$ in which case the matcher 3 must have an impedance $Z_3<Z_o$, as may be inferred from the work of Khuri-Yakub et al (1988) reviewed in applicant's aforementioned book, at page 125.

In the embodiment of FIG. 1, the impedance-varying isolation rings or spiral are placed along the conduit, which thus contains the signal isolation structure, while the transducer housing is devoted to structural or impedance matching elements for launching the acoustic signal into a gas. The principles embodied in FIG. 1 are further illustrated in another assembly. In FIG. 1A, the path of interrogation is folded along a U-shaped channel. The bottom leg of the U-shape is substantially massive and includes two 45 degree reflecting surfaces. The side legs of the U-shape are thin-walled, typically 10 mils or ¼ mm, of SS316, welded at each end into more massive sections. Massive rings are clamped at intervals and these collars, corresponding to rings 10 and 11 in FIG. 1, are preferably alternately rotated 90 degrees to interrupt the thin-wall path as much as possible.

Each transducer assembly in FIG. 1A includes a quarter-wave matcher 3 epoxied directly to the membrane corresponding to 4 in FIG. 1. This holds the membrane in place aven under evacuation of the cell. The transducer housing is backed to resist high gas pressure in the cell, equivalent to what is shown in FIG. 1, except that the gland and lock nut are of somewhat different design. A backup seal consisting of an attenuating O-ring of silicone or fluorosilicone may be captured betwween the transducer housing and the nearby cylindrical wall. In MOCVD (metalorganic chemical vapor deposition) applications, it is common practice to maintain the temperature of cells by immersing them in a water bath whose temperature is kept constant to the order of 0.1 degree C or better. When the cell of FIG. 1A is to be immersed in such a bath, a plastic wrap is used to prevent water from short circuiting the isolation means. This may be shrink wrap.

Figure 2A:
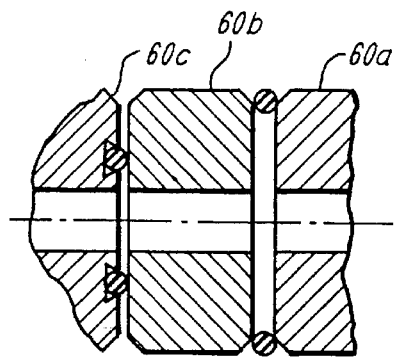
FIG. 2A illustrates a method of ring spacing.
Figure 2:
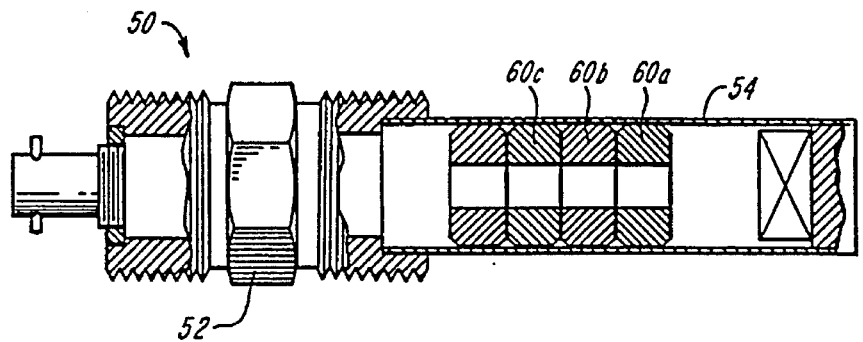
FIG. 2 shows a cross-sectional view of another transducer assembly in accordance with the present invention.

FIG. 2 shows a different embodiment, wherein the transducer housing itself contains the isolation structure.

In this embodiment a transducer assembly 50 includes a threaded base 52 that secures a titanium or stainless steel thin-walled cylindrical housing 54 approximately ten to twenty mils thick, having a signal-transducing crystal 56 mounted at its tip followed by suitable coupling, impedance matching and sealing elements as described in connection with FIG. 1. When the base 52 is screwed into a mounting hole, the crystal end projects into the stack or conduit. Located within the thin-walled transducer housing 54 are a plurality of massive titanium steel or carbon steel rings 60a, 60b, 60c which are press-fit in position spaced apart slightly by interposing silicone O-rings of approximately one sixteenth inch cross section. The rings may be welded. Each ring is chamfered to facilitate insertion, and has an aperture through its center for passage of transducer wires. Each ring is approximately 0.25 to 0.50 inches thick and its edges are chamfered 0.06 inches by 45°. One or more dimples alternatively may be made on each axially-directed face of the inserts, e.g., with a prick punch, and the inserts would then be pressed together so that they actually contact each other at most only at the dimples, and remain essentially acoustically isolated from each other except via the thin walled shell. This assures that the acoustic path between the transducer crystal and the transducer's point of attachment to the stack or conduit passes through an alternating series of massive elements. While four rings are shown, the invention contemplates generally three to six such elements, the number varying with the application and being generally selected based upon considerations of the desired transducer size and weight, allowable insertion loss, and the like, as discussed further below. The gaps between rings may also be configured as shown in FIG. 4.

Figure 3:
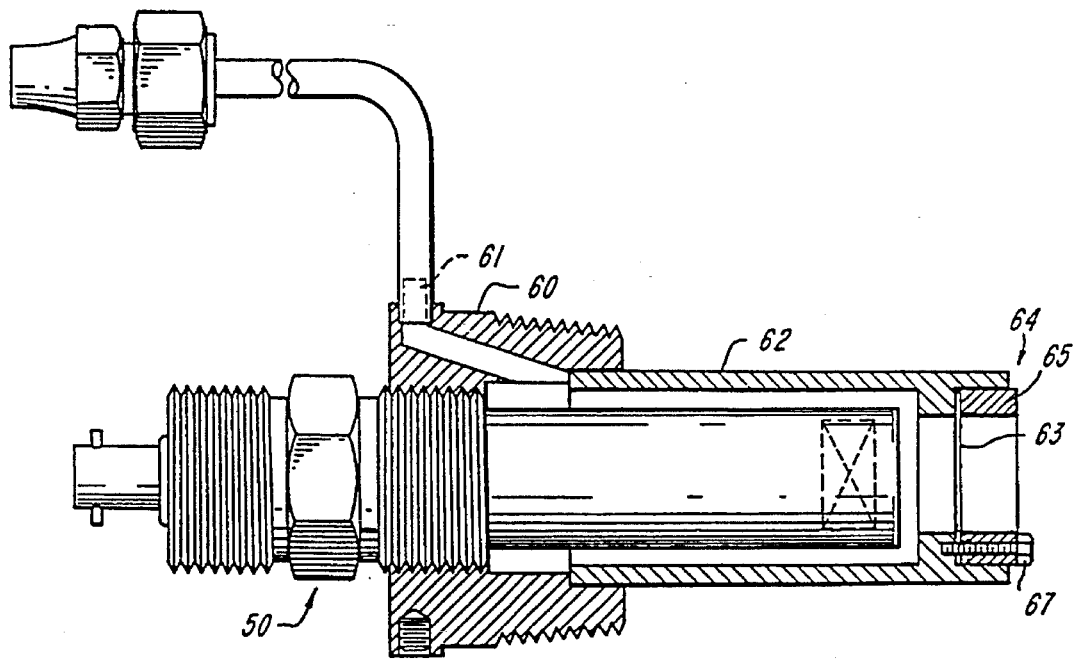
FIG. 3 shows the assembly of FIG. 2 in a high temperature mounting.

FIG. 3 shows the transducer assembly 50 of FIG. 2 mounted for interrogating a flow of stack gas or other high temperature fluid. The previously described sensor structure 50 is mounted within an external mounting assembly comprised of a base 60, and a surrounding sleeve or shell 62 and protective end cap 64, which together define a jacket for a flow of cooling/purge air through passage 61, and via cap 64 into the sensed fluid streams. Cap 64 may include for example, one or more nickel, stainless steel or plated graphite screens 63 secured by a mounting ring 65, which in turn is affixed with cap screws 67. The purge gas may be ambient air or other gas (e.g., $N_2$), may be cooled or heated, and may be directed to flow right over the transducer face, or prevented from doing so and instead be returned to the source area outside the nozzle or stack. Each transducer may have more than one purge line, activated by time, temperature, manual override or signal degradation.

In some installations it is important to be able to remove the transducer assembly without depressurizing the pipe, and without incurring the cost of leaving an "isolation valve" permanently installed at each nozzle. One way of satisfying this requirement is indicated in FIG. 4. Here a nozzle extension 110 is removably attached by means of a removable ball valve 100 (shown in dashed lines to emphasize its non-permanent status) to a nozzle 90 that is welded to the pipe. The nozzle and nozzle extension are coaxially bored through to a diameter $D_R$ and the ball valve has a passageway when open of at least $D_R$. A gland 80 is attached to or is part of the transducer assembly. The gland contains sealing means, illustrated as an O-ring 82 or other packing means, and is installed or removed by connecting an insertion or removal tool to the threads 84 shown at one end, or by other similar mechanical attachment. In the embodiment illustrated, the transducer assembly is installed in a slightly recessed position. Potting material 86 absorbs the ringdown within the transducer's isolation structure. The acoustic masses are coupled to the thin-wall sleeve by circumferential welds, which Applicant has found to constitute a practical joint, fabricable by electron beam welding. Alternatives include brazing or provision of epoxy between the acoustic masses and the surrounding thin-wall sleeve.

Figure 4:
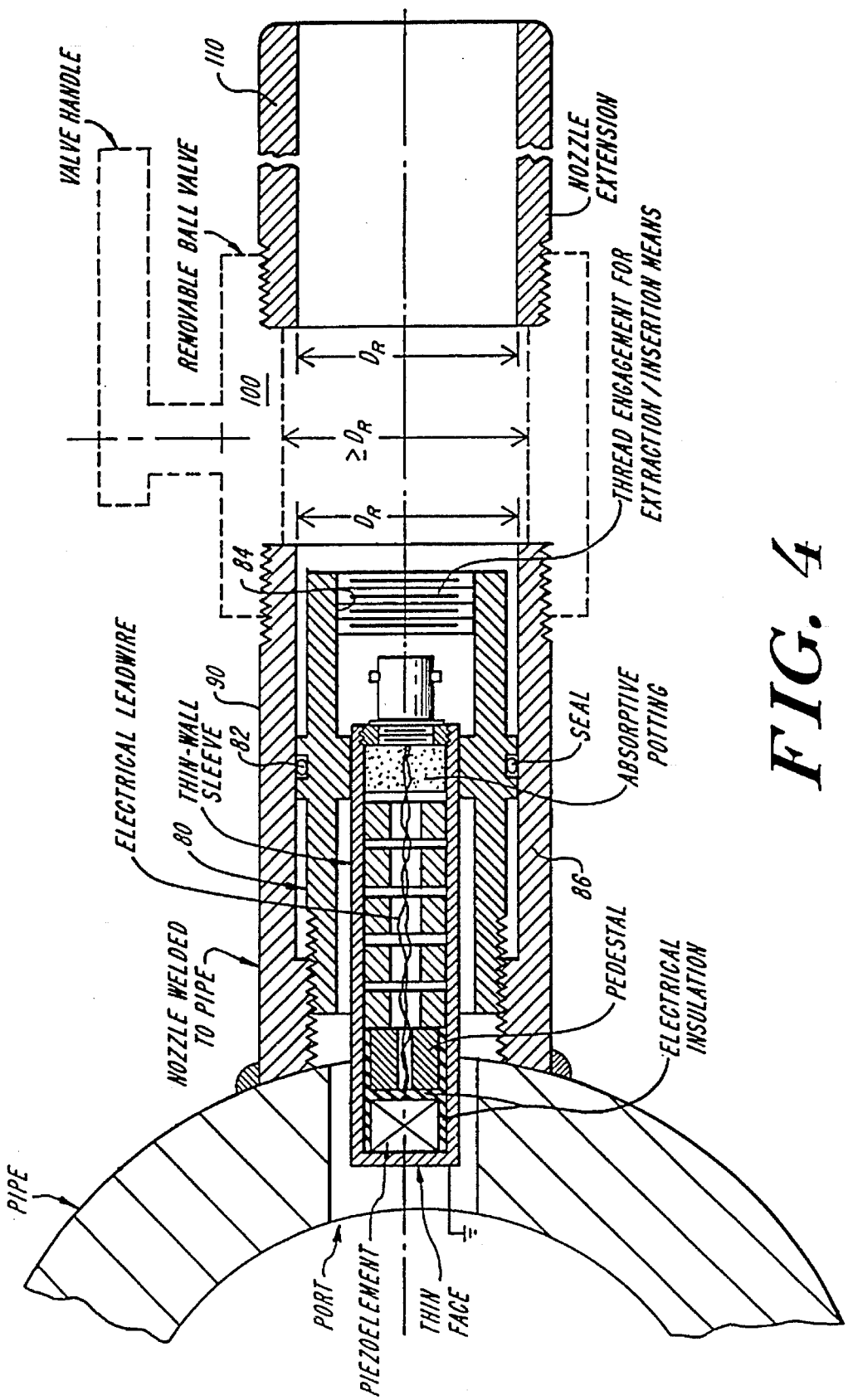
FIG. 4 shows an embodiment of the invention adapted to be removably placed in a valved pipe nozzle.
Figure 5:
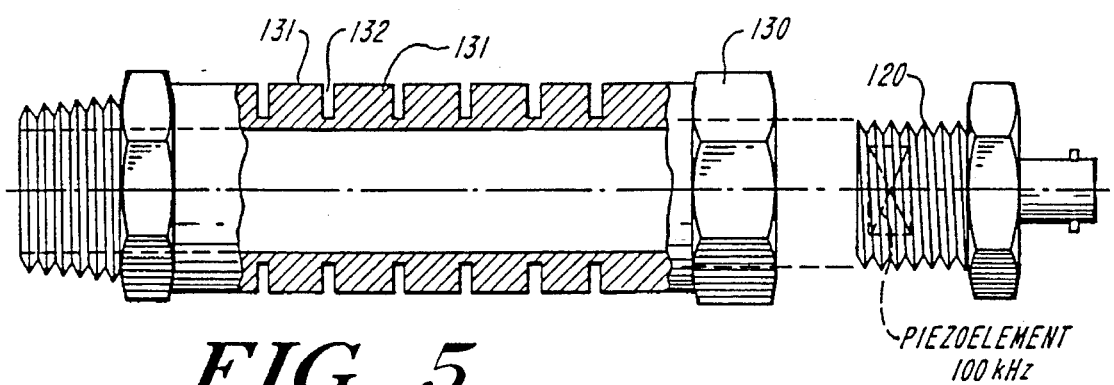
FIGS. 5 and 6 show isolator bodies interposed between a transducer and a conduit.

In the designs of FIGS. 2–4 discussed so far, the isolation structure consisting of alternating hi Z, lo Z (where Z indicates the acoustic impedance) has been permanently built onto the transducer assembly. To facilitate repair of the transducer, and to reduce inventory and possibly fabrication costs in some instances, it may be desirable to separate the piezoelectric element from the hi Z, lo Z structure. One way to accomplish such separation of elements is shown in FIG. 5.

Here the transducer housing 120 contains the piezoelectric crystal, mounted against a membrane front face such as a steel membrane of thickness 50 mm to 250 mm, which Applicant has found appropriate for frequencies on the order of 100 kHz. As before, a quarter-wave impedance matcher may be installed between the piezo element and the thin window. The transducer housing 120 screws into a separate isolator section 130, and the isolator 130, in turn, screws into the nozzle on the pipe or stack. The isolator specifically includes a multiplicity of impedance mismatches created by alternating acoustic masses 13 1 and gaps 132. The gaps 132 may be on the outside or inside of the isolator, the former choice being illustrated on FIG. 5. The number of interruptions in the conduit wall that are required to achieve an effective level of attenuation depends on the application, i.e., on the gas impedance and pipe material and geometry. In a very large steel pipe, say one meter in diameter filled with ordinary air, the transit time across the air diameter path at 20 degrees Celsius is about 3 ms. In this amount of time the short circuit or crosstalk decays quite a bit at 100 kHz, and so only a few sections of hi Z, lo Z conduit mismatch are required. But for a small steel pipe, of about 50 mm diameter, the transit time for air at room temperatures is only about 0.05 m/343 m/s=150 ms. In this case, about six sections are required, three on each side of the path, to achieve adequate attenuation of the solid-borne noise. These illustrative numerical examples apply for transducers radiating through very thin diaphragms, a construction in which the diaphragms also contribute to the isolation, If thicker windows are used, more isolation is required in the hi Z, lo Z structure.

Figure 6:
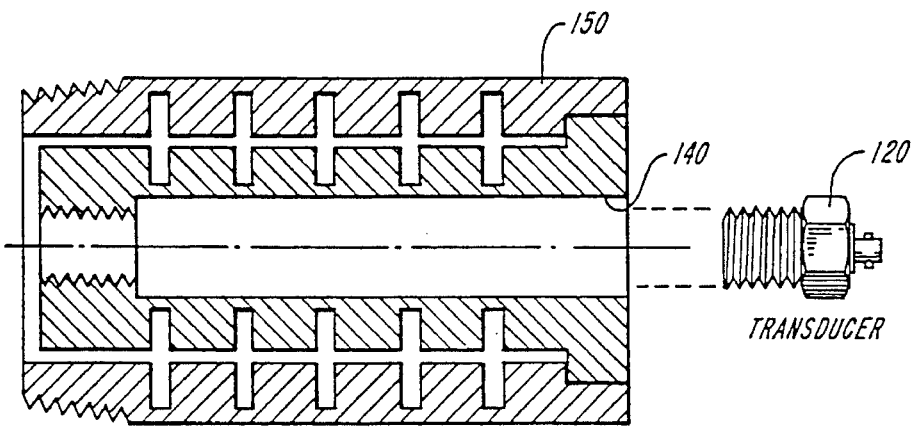

In cases where many sections of hi Z, lo Z appear necessary but where space is restricted in the nozzle's axial direction, a reentrant isolator structure may be employed, as illustrated in FIG. 6. In this embodiment the transducer 120 is mounted at the end of one leg 140 of the isolator structure, and the far end of the other leg 150 attaches to the conduit. Each leg has a structure of alternating impedance mismatches resulting from radially-oriented circumferential slots. As shown, the irregular slotted surfaces of the two legs are essentially enclosed by the legs themselves, rendering the structure largely resistant to clogging accumulations.

Unlike structures of packing washers or the like which have previously been used to isolate transducers, this new structure can be used in a steam environment without waterlogging, deteriorating or changing its properties, and is composed entirely of perfectly elastic, rather than viscoelastic elements.

Viewed as a function of distance along the housing or conduit from the transducer crystal, the acoustic impedance of the isolation structures described herein will be seen to have the profile of a square wave, with a peak-to-valley ratio corresponding to the thickness of the original stock and the depth of the isolating slots 132 (FIG. 5). Preferably this impedance alternation ratio is over 3:1, and more preferably, greater than 6:1.

Figure 7:
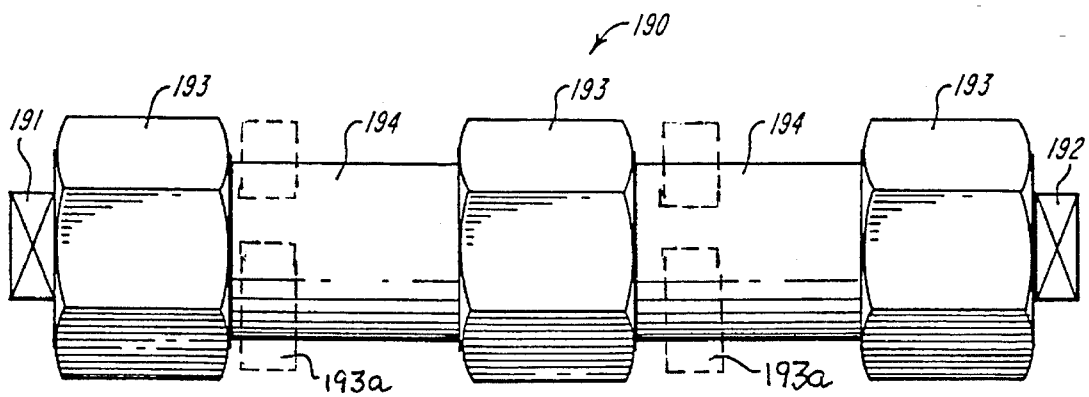
FIGS. 7 and 7A show an isolator body incorporated in a sensing conduit, and show signal characteristics thereof, respectively.
Figure 7A:
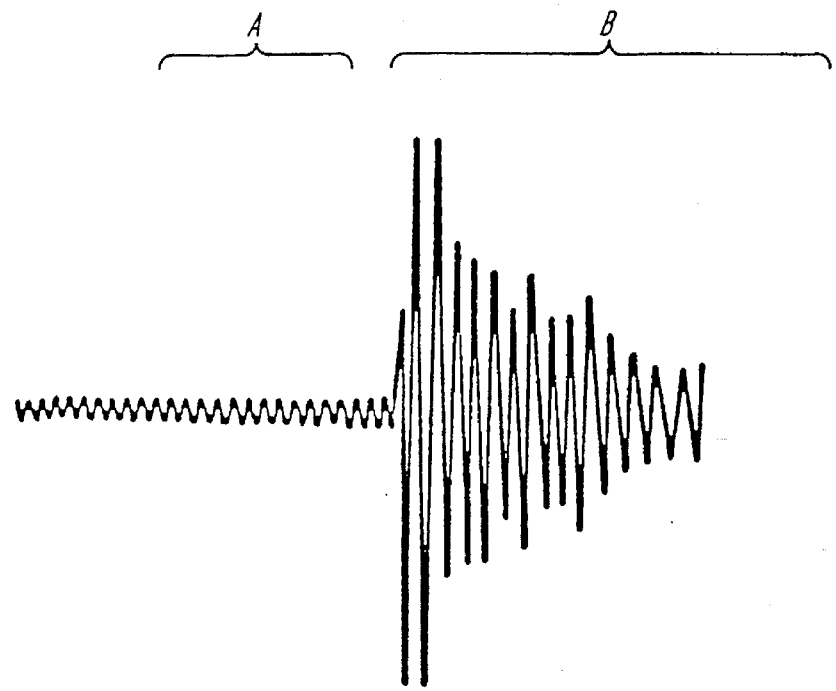
Figure 7B:
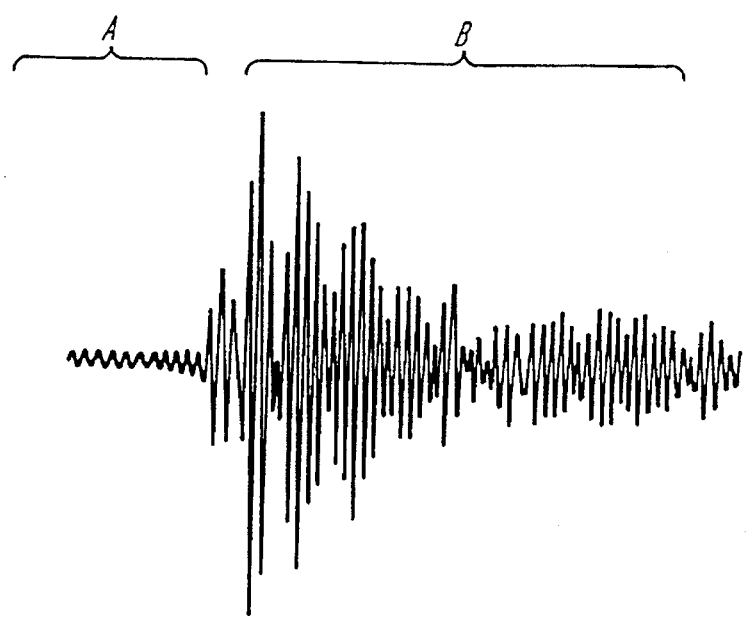
FIG. 7B shows a signal trace for the flow cell of FIG. 1A.

This aspect of the invention may also be implemented using conventional conduits and fittings in a variety of ways. For example, a structure wherein the alternating masses are placed about the conduit between two transducers, rather than between a transducer crystal and the conduit, may be constructed as shown in FIG. 7. In this system 190, a pair of opposed transducers 191, 192 launch and receive signals through a fluid path constrained by a conduit formed of alternating segments of 1½ inch high pressure pipe couplings 193 and six inch lengths of pipe 194, the couplings having a much greater wall thickness and acoustic impedance than the pipe lengths. FIG. 7A shows an oscillogram of a received signal propagated through air in the isolator conduit embodiment of FIG. 7, indicating the very low level of crosstalk (region A) and the well defined transmitted signal (region B). Depending on gas pressure, the pipes 194 may be thinned and massive collars (shown dashed, 193a, b) may be clamped thereto, to achieve SNR (signal to noise ratios) in excess of 100:1. An actual test result for the U-shaped cell of FIG. 1A is shown in FIG. 7B, for which the SNR is on the order of 100:1.

To quantify the nature of impedance mismatch created by the alternating masses and their effect on particular signals, one must deal with the wave impedance, and that means knowing exactly what the wave of interest is, which is to be isolated or blocked by successive mismatches. For many of the frequencies and dimensions of concern here, not just one wave but several are involved, including different modes, e.g., symmetric and asymmetric plate waves. Although one may not know the exact formula for impedance for each wave mode of interest, one can make the assumption that the magnitude of the wave impedance is proportional to the mass per unit area in a plane perpendicular to the axis of the isolator section. This means that one can represent the impedance function like a square wave drawn on a graph of mass per unit area (y-axis) against axial dimension (x-axis). In the "square wave" the peaks and valleys do not need to have equal durations; applicant has found that very small gaps between masses suffice.

Unlike typical impedance mismatches in the prior art of Livengood et al. consisting of alternating materials such as asbestos-like gaskets sandwiched between steel washers, the present case involves lo Z, hi Z steps created by differing amounts of essentially the same materials, typically the same or different metals. This new alternation is amenable to sandwiching masses between concentric thin wall sleeves and thus the lo Z parts are sealable against water or ice and thereby made weatherproof. In contrast, prior-art gasket isolators are subject to being compromised by moisture from weather or other sensed environment, such as steam encountered in steam flowmeters.

Intuitively one might expect that the greater the number or magnitude of Z steps in the square wave, the better the isolator becomes. This turns out to not always be true. In order to optimize the isolator with respect to specific requirements such as minimum weight, minimum length, etc., applicant offers an analysis based on a simple form of the energy transmission equation, $T=4r/(r+1)(r+1)$ where r is the ratio of impedances of the small and large mass sections. A few numerical examples will help explain the optimization found by the applicant, as set forth in the following table, Table I.

TABLE I

| r | T | INSERTION LOSS, 10 log T,db | IL/r, dB/Section |
|---|---|---|---|
| 1 | 1 | 0 | 0 |
| 2 | .889 | .51 | .255 |
| 3 | .750 | 1.25 | .417 |
| 4 | .640 | 1.94 | .485 |
| 5 | .556 | 2.55 | .510 |
| 5.8 | .501 | 3.00 | .516 |
| 6 | .490 | 3.10 | .517 |
| 7 | .438 | 3.59 | .513 |
| 10 | .331 | 4.81 | .481 |
| 14 | .249 | 6.04 | .431 |
| 20 | .181 | 7.41 | .371 |
| 30 | .125 | 9.04 | .301 |
| 38 | .100 | 10.00 | .263 |
| 50 | .077 | 11.14 | .223 |

Table I shows several interesting points. First, as the impedance peak/valley ratio, r, increases, the insertion loss (IL) increases, but not linearly. This is seen from the fact that values of r=6, 14 and 38 yield IL's of approximately 3, 6 and 10 dB, respectively. Second, to get a "useful" insertion loss of at least 3 dB, one requires a value of r≧5.81. Third, to achieve a particular level of insertion loss it is not immediately apparent whether it is "better" to use a large r or two sections each having half that value of r. For example, r=4 yields more insertion loss that two sections with r=2. Likewise r=6 yields more than two sections of r=3. But r=10 does not yield more than two sections of r=5. This means that if a particular level of IL is required, and if the solution must not exceed a particular weight limit, one cannot simply choose a very large r. It may be necessary to use n sections of an intermediate r value, such that $(n \times IL_0)/(n \times r_0) = IL_0/r_0$ is maximum or near-maximum. The last column of Table I shows that IL/r appears maximized when r is about 6. If other conditions allow it, this choice of r is preferred, because it allows a given IL to be achieved at minimum mass, for IL.>3 dB.

It is to be understood that the number of sections may be comprised all in one transducer, shared between two transducers, or shared among transducers and separate "isolator" sections formed in or on a mounting, or about the conduit.

The invention also contemplates the incorporation of isolated transducers directly into equipment other than ducts. For example, the transducers can be installed in valve bodies, preferably upstream from the valve mechanism. The elimination of crosstalk makes it possible for isolated transducers of the present invention to achieve highly accurate measurements in diverse such structures without requiring specially designed flow cells and custom mounting.

Figure 8:
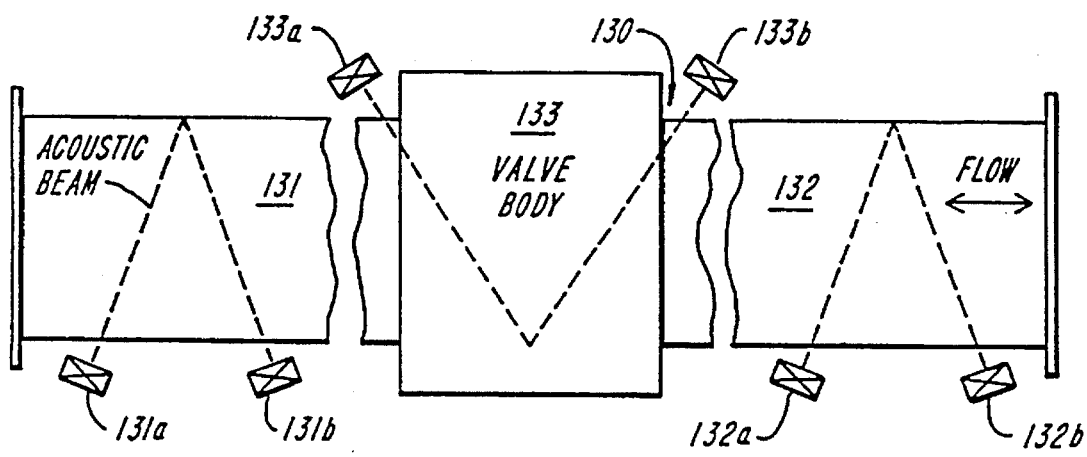
FIG. 8 shows an isolation mounting in a conduit reflected wave system.

FIG. 8 illustrates such a system 130 wherein left and right flow segments 13 1,132 lead through a valve body 133, and each segment is provided with a pair of isolated transducers 131a, 131b or 132a, 132b for detecting flow in the segment. In this embodiment, bidirectional flow is contemplated, and instrumentation preferably responds to the direction of flow by selecting the pair of transducers which are upstream of the valve body to conduct flow measurements. In cases where minimum length is absolutely necessary, it may be possible to straddle the valve mechanism with a pair of transducers 133a, 133b. Readings in this case may be possible in only some of the setting positions of the valve mechanism, depending on the extent to which the mechanism interferes with the acoustic beam path between this transducer pair.

Returning now to the constructions of FIGS. 1 and 2 involving a thin diaphragm or window, certain preferred constructions are proposed for reasons of safety to deal with either an occasional or accidental overpressure event in the sensed fluid.

Figure 9:
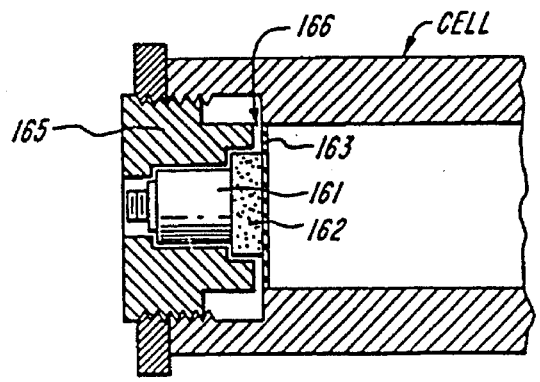
FIGS. 9, 9A show constructions in which transducer coupling to the fluid or housing varies with changing fluid conditions.

In one variation of the transducer mounting, a support is provided that is slightly spaced, by about one mil, from the diaphragm end window. FIG. 9 shows such an embodiment 160, wherein a transducer crystal 161 attaches, via a λ/4 matching block 162, to a diaphragm 163 which normally is spaced one mil from a supporting body 165 at gap 166. Thus, at low pressure in what we may take as normal operating conditions, the support means does not come into play and so does not introduce acoustic crosstalk. In these conditions the gas pressure is so low as to yield only weak ultrasonic signals, the detection of which would be jeopardized by strong crosstalk. But when pressure becomes high, the support 165 limits the motion of the diaphragm to safe excursions by bearing against the diaphragm. In so doing, crosstalk is increased, but at the same time the signal strength increases due to better match between transducer and gas impedance. Hence the signal to noise ratio can still be high enough to allow useful measurements. The effect of residual crosstalk can be reduced by recording it as a function of pressure and/or temperature, and then subtracting the recorded values from the resultant (signal+noise) detected signal. The increased signal, whose amplitude increases nearly in proportion to gas pressure, will be noted later on in sensor configurations that sense gas density or gas pressure.

Figure 9A:
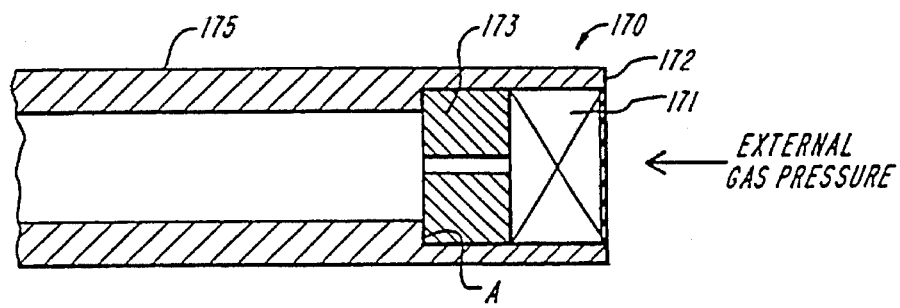

FIG. 9A shows an adaptation of the construction of FIG. 8 to an isolated transducer housing and mount 170. Transducer crystal 171 is coupled to a diaphragm 172 by a couplant, and a pedestal 173 almost spans the cavity between the other side of the crystal 171 and a shoulder of the thin-walled cylindrical isolation section 175 which is for example, similar to that of FIG. 2. As the gas pressure in the sensing chamber to the right of the crystal rises, pressure builds up at shoulder "A", allowing the crosstalk to increase under the high pressure conditions in which adequate signal strength is achieved. The transducer is thus enabled to operate faithfully over a broad range of pressure conditions. In some situations, the crosstalk amplitude may be taken as a measure of gas pressure. This may be understood from prior art work of Crecraft or the applicant, ca. 1964, in which pressure coupling between solids was found to increase approximately in proportion to pressure at least for pressures up to around 1000 psig.

One embodiment of the foregoing construction is especially applicable to a low impedance gas, for example, in aerospace situations where gaseous hydrogen or other gaseous cryogens are involved. In these cases, one of the collateral problems is coupling the piezoelectric element to the window. Bonding sometimes works, but because of differential expansion coefficients it is advantageous to have some degree of flexibility in the couplant. There seem to be so far no really "flexible" couplants known or available to function at temperatures of liquid nitrogen (–196° C.) and below. Applicant has found, however, that the anti-gall compound sold under the trademark Never-Seez [manufactured by Never-Seez Compound Corp., Broadview, Ill. ] can be applied between two surfaces at room temperature, squeezed thin and then it couples ultrasound well at room temperature and also at –196° C. Hence this compound can be introduced as a couplant between the crystal and the end window in the isolated transducer designs shown herein, to operate when the application spans all the way down to cryogenic levels. The Never-Seez material was developed for use at high temperatures, over 1000° C., so this one couplant will operate at both extremes of temperature. A conservative transducer rating would be ±200° or ±250° C. Applicant has identified a second anti-gall compound, sold under the trade name Permatex, Part No. 133K, made by Loctite of Cleveland, Ohio, which is also normally intended for high temperatures, and this too is useful as a cryogenic couplant that can be applied at room temperature. Other suitable cryocouplants may be found among "anti-gall" lubricating compounds.

Another factor addressed by subsidiary aspects of the invention relates more to high temperature gas flows. When transducers made according to this invention are installed in pipes at temperature extremes, the angle that the transducer axis is to make with the pipe depends in part on whether the objective is to have the sound beam's transit time be influenced by flow, or not be so influenced. To be immune to flow, e.g., to measure density or the like, installation would typically be perpendicular to the pipe axis. But if one wants to measure flow by the contrapropagation method (as described for example in applicant's book, Ultrasonic Measurements for Process Control, Academic Press 1989, chap. 4), the usual method is to install transducers at 45 degrees to the flow axis. However, at temperature extremes, if the transducer is recessed in a nozzle, this creates a still region or refraction wedge where the nozzle port enters the freestream, that can significantly divert the propagation path.

To minimize refraction, applicant recognizes that the angle of incidence should be as near zero as practical. On the other hand, too small an angle means that the small upstream-downstream path component results in a time difference that generally is too small to be measured accurately. Ideally one would like to use normal incidence, thereby avoiding the refracting wedge at temperature extremes, and yet achieve a useful propagation path component L>zero. Applicant has found that at 100 kHz, where commercially available ultrasonic flowmeters such as the Panametrics model GP68 can resolve delta t to 10 ns, a useful minimum delta t is 1 µs, where delta $t=2LV/c^2$. (This sensitivity corresponds to flow resolution of 1%.) In large pipes of diameter D>300 mm at high flow velocities, it often turns out that an L of a few centimeters suffices, say L=3 cm=30 mm. Thus L/D may be on the order of 30 mm/300 mm=0.1. Now if the half-angle of the ultrasonic beam in radians measured at the −3 dB points exceeds L/D, normal incidence can be used, and the transducers can simply be installed offset by the axial distance L. This simplification is important with respect to safe hot tapping and nozzle attachment, since these installation operations are greatly simplified at normal incidence.

Figure 10:
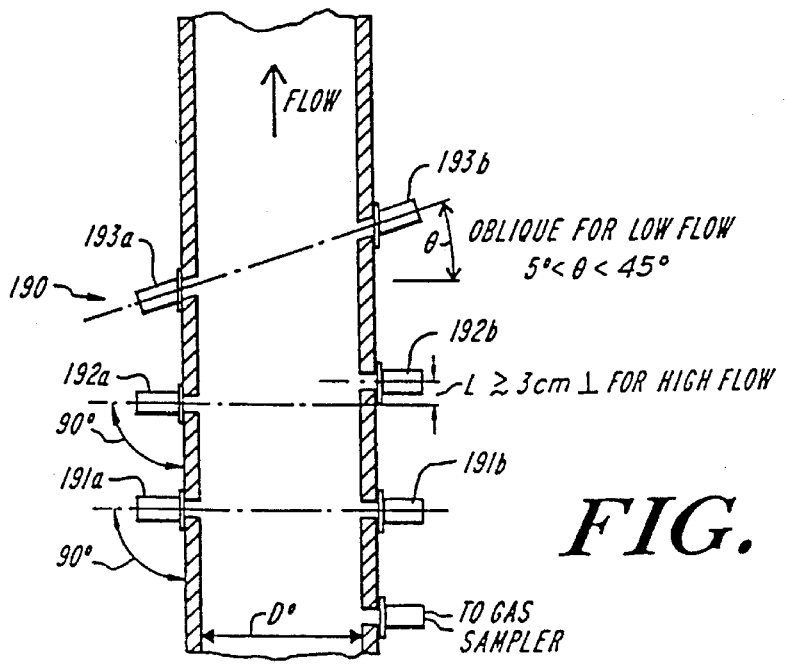
FIG. 10 illustrates slant and offset mounting geometries of transducers in systems according to the present invention.

In cases where both low and high flows can occur, all at high temperature, for example, the invention further contemplates providing multiple sets of ports. As shown in FIG. 10, the ports for high velocity 191a, 191b, 192a, 192b can be at normal incidence, while the ones for low velocity can be oblique because at low velocity the refracting wedge is not so distinct since the freestream temperature tends to penetrate into the port.

When using the flow-cooled transducer of FIG. 3 at low flows, the Bernouli effect may not be sufficient to draw cooling air into the free stream and thereby provide self-cooling and self-purging. In other cases air may be a hazardous or disturbing addition to the composition of the measured gas in the stack. In such cases a positive flow of an acceptable, perhaps inert, gas, e.g., pressurized nitrogen, may be introduced as a preferred purge gas.

In still other cases, as where an electric arc is to be extinguished, sulfur hexafluoride may be the preferred purge gas. In one example of such a case, a minimum mass flow of $SF_6$ must be valved into lower-pressure lines, and it is necessary (in one application in which 362 kV and 800 kV double pressure circuit breakers are employed) to ultrasonically verify within 60 ms that the required flow has occurred, or else a safety circuit triggers other more disruptive protective devices. In this application the flow is both transient and turbulent, and it is difficult to measure the flow velocity accurately in so short a time. Applicant proposes to measure such flow indirectly, by instead ultrasonically measuring the temperature change in the gas based on sound speed (as described in applicant's aforesaid book, chap. 5). Here the temperature is measured over one or more paths to obtain a meaningful average temperature, which, integrated over time, provides a measure of the change in gas mass remaining in the supply reservoir. The transducers for such applications where the conduit is already all welded together in an existing plant, are preferably of the clamp-on type. But when such gas conduit systems are designed with ultrasonic interrogation in mind, one can provide for transducers or conduits with the isolated design of the present invention. This is expected to yield higher accuracy than obtainable with clamp-on transducers. In some cases, one transducer can be clamped on, and the other remain "wetted," provided all the necessary isolation can be achieved in the "wetted" transducer or between the two transducers.

Figure 11:
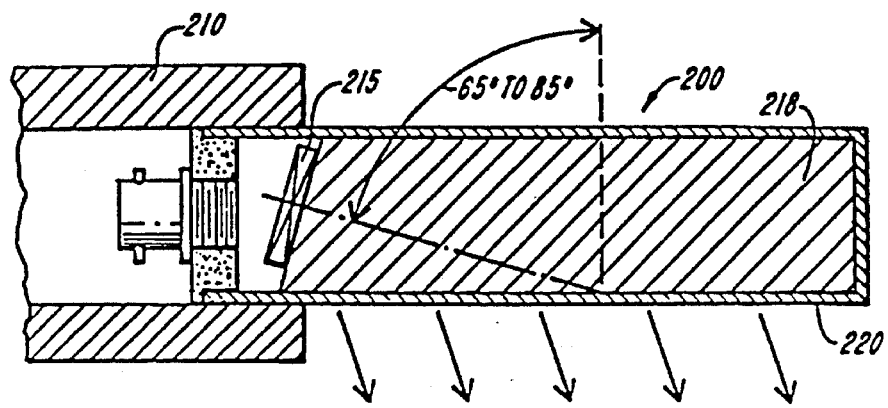
FIG. 11 illustrates a transducer structure for use with low impedance media.

FIG. 11 illustrates another embodiment for an isolation-mounted transducer 200. In this embodiment, an alternating-impedance isolation body 210 is interposed between the transducer crystal 215 and the solid body path of the conduit walls, and the crystal radiates at grazing incidence to excite a thin-walled extended source 220 that radiates or receives the ultrasonic interrogation wave through a surrounding medium. The thin-walled source 220 is thin compared to the wavelength, e.g. preferably under µ/10 and no more than µ/2 thick, and is preferably stainless steel containing a wedge 218 made of a low sound-speed material such as CMG or ATJ graphite, or chalcogenide glasses or plastics. The low sound speed contributes to a large refracted angle according to Snell's law. On the other hand if a small refracted angle is sought, then a high sound speed material is preferred, e.g., alumina, beryllia or perhaps beryllium.

Figure 12:
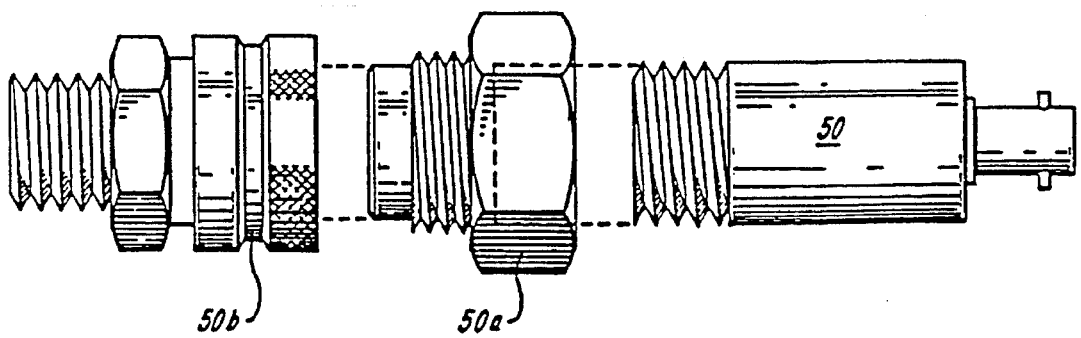
FIG. 12 illustrates a quick-connect embodiment of the invention.

In many of the above-described applications, it is desirable to perform several occasional sets of measurements on a conduit, without any continuing need to monitor fluid parameters, or, as in FIG. 10, one desires to place the transducers at different positions depending on present flow levels. For these applications applicant proposes a conduit-to-transducer mounting as shown in FIG. 12. In this embodiment a isolation-mounted transducer assembly 50 is provided with a quick-disconnect stem fitting 50a, and a corresponding quick-disconnect body 50b is fitted to the conduit or reservoir wall. Suitable interconnecting body and stem parts are, for example, are Swagelok fittings SS-QF-12-B-12-PM and SS-QF-12-S-12-PF. For lower pressure applications, the transducer assembly need not be provided with such secure pressure fittings, and the corresponding mounting may comprise simply a precision bored nozzle and closely fitted cylindrical transducer body which is simply placed in the nozzle bore and positioned or retained by a spring-loaded ball detent. The quick-connect may have an automatic shut-off, or alternatively a plug may be used when the transducer is out.

The foregoing examples illustrate solid body attenuators in which elastic elements-alternate metal rings and thin shells in series-attenuate noise transmission.

It is also possible to provide a relatively simple isolation structure in which O-rings made of attenuating material are lightly sandwiched with low contact force about a steel or highly elastic flange or even a strong plastic solid body. Furthermore, hybrid constructions are possible wherein a conduit or gas measurement chamber is formed of a very thin and structurally indefinite wall—for example a metal bellows—while a separate frame or outer housing provides dimensional precision and structural rigidity to secure the transducers in defined positions. Each of these constructions will be further discussed below.

Figure 13:
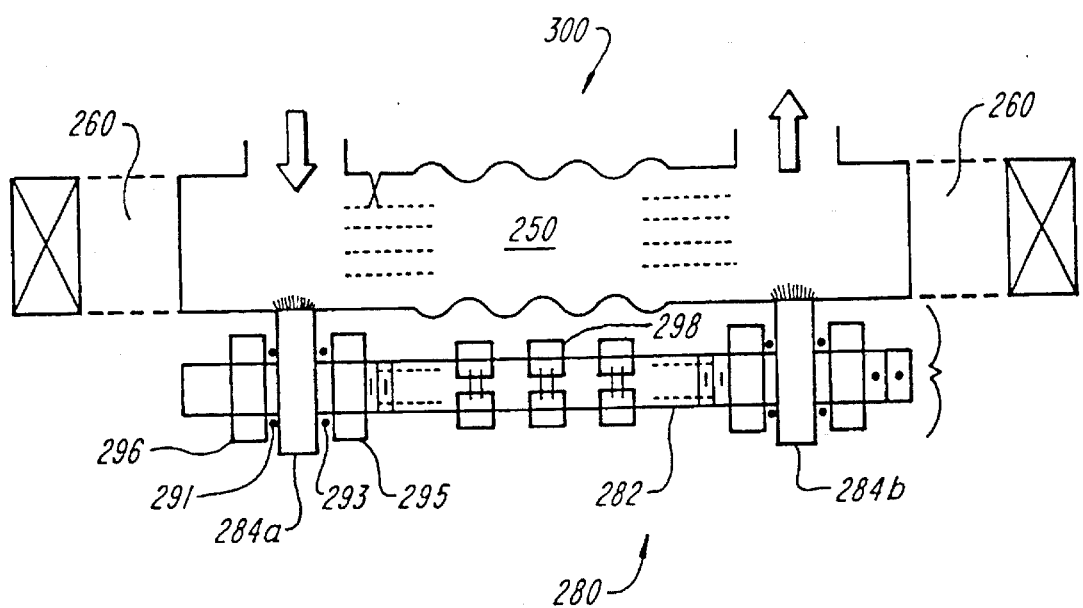
FIGS. 13 and 14 illustrate hybrid systems with separate acoustic and structural isolation sections.

FIG. 13 shows a hybrid system 300 comprised of two major elements, a thin walled containment vessel 250 and a rigid frame 280. Frame 280 consists of a first yoke 284a fitted to one end of the vessel 250, and a second yoke 284b fitted to the other end of vessel 250, with the two yokes being rigidly spaced apart by an elongated rail or body 282. A₀ transducer 260 is fitted into each yoke and directed along the axis of the containment vessel 250. Vessel 250 is a limp and flexible tube, preferably corrugated, and having a very thin wall such that the product of its thickness with the signal frequency (corresponding to the lowest order flexural wave ($a_o$) speed in the material) is low, e.g., below 1 MHz.mm. This assures that the noise in vessel 250 travels more slowly than the gas-carried signal, so that the measurement signal may be detected before ringing commences.

As illustrated in the cross-sectional details of FIG. 13, each of the solid frame members constituting a yoke 284a, 284b is secured to the rail 282 by being clamped between a first and second O-ring 291,293, with rigid plates or collars 295,296 tightened against them to securely fix the position of the yoke. The corrugated bellows 250 is rigidly attached to the yoke at each end, preferably by brazing or with a sealing ferrule, gasket or sealing material. Suitable flexible tube assemblies are available from The Cajon Company, a division of The Swagelok Company, of Macedonia, Ohio as their 321SS flexible stainless steel tubing, and are available with glass or weldable metal end fittings. These bellows are suitable for relatively low pressure gas measurement applications. Preferably a system for general use in the chemical process industries and for many metalorganic chemical vapor deposition processes would utilize a bellows or corrugated tube of 316 stainless steel, rather than the common commercial 321SS product.

The selection of O-ring material requires some care. Preferably the O-rings are formed of material which is acoustically attenuating and suitable for the intended chemical and thermal environment. Applicant has found silicone, fluorosilicone, neoprene and Buna-N to be suitable materials, with fluorosilicones offering excellent resistance to high temperatures and hydrocarbons. Several common O-ring materials, notably Teflon and Viton, were found to provide very poor isolation and to be unsuitable. The O-ring thickness also requires careful selection. For example, on the assembly of FIG. 13, with O-rings fitted about a ten millimeter diameter rod 282, a silicone O-ring 2.3 mm thick provided best isolation, whereas a ring twice as thick of Neoprene or Buna-N was required. In each case, the ring was tightened to a less compressed state than is customary when O-rings are used for sealing. For example, a compression of well under forty percent, and preferably about ten percent is suitable, with care being taken that the solid frame 284 and mounting plates 295,296 do not contact each other. A thin wire or protrusion may be brazed to the surface of the plates 295, 296 to act as limit stops. Other isolation means as described above are also shown applied to the rail 282 to further cut down on acoustic short circuiting. For example, as shown in the embodiment of FIG. 13, a plurality of massive damping rings 298 are spaced along the rail 282.

Figure 14:
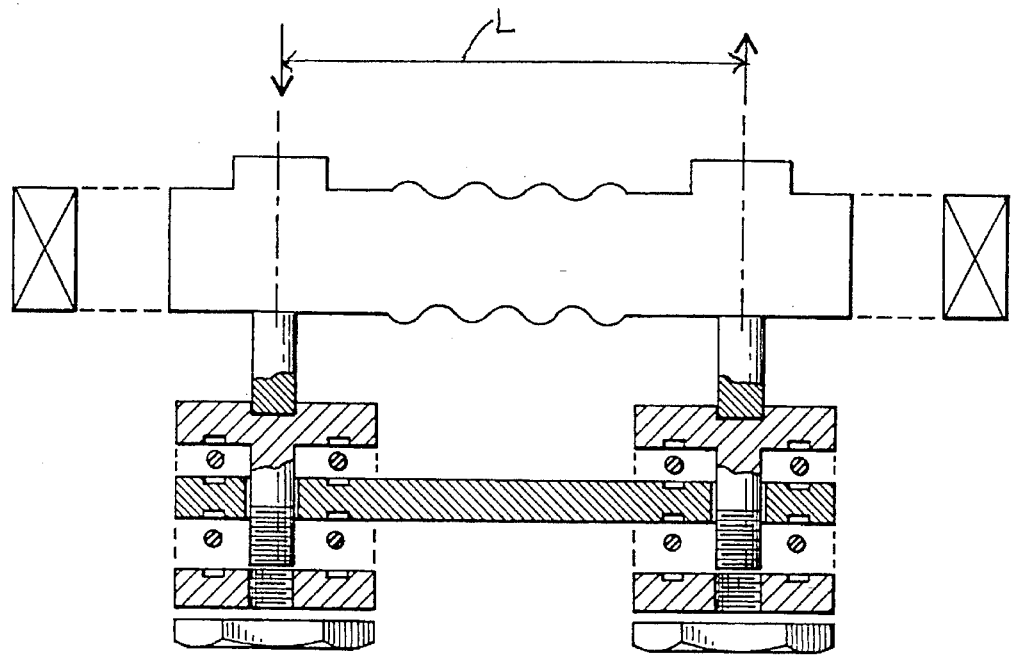

FIG. 14 shows a related O-ring isolation construction in which a dimensionally stable mounting plate is isolated by O-rings from a pair of end posts that hold the bellows.

As was the case with the massive damping rings, this O-ring isolation structure may also be applied directly to the transducers.

Figure 15:
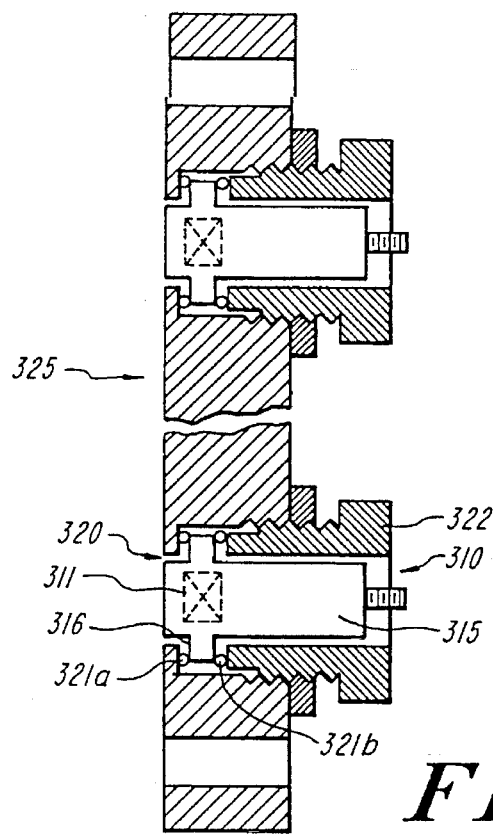
FIG. 15 illustrates transducer isolation with an O-ring sandwiched flange.

FIG. 15 shows such a construction, wherein a transducer 310 including a crystal 311 and suitable coupling and diaphragm are mounted in a small cartridge-like housing or case 315 having a flange 316. The case 315 is fitted into a bore 320 in a conduit or chamber, with the flange sandwiched between a pair of O-rings 321a, 321b. A gland or packing nut 322 tightens the assembly down, allowing secure fixation and slight positional adjustment along the transducer axis. In this manner the transducer itself is isolated from the solid body of the fluid-containing structure. As shown in this illustration, this isolation mount is particularly compact, allowing two or more transducers to be placed adjacent to each other in separate bores in a single solid body 325, which may, for example be the wall of a thick-walled pipe, a plug, or a pipe flange or flange cover as illustrated. The lock nuts, if used, are tightened after the gland is tightened.

Figure 15A:
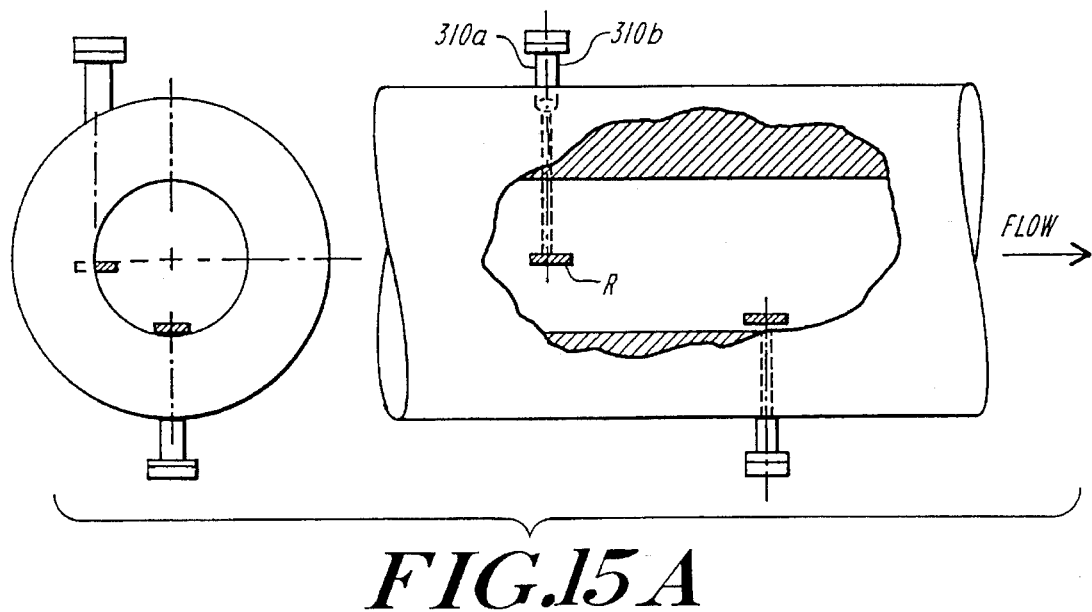
FIGS. 15A–15D illustrate systems using O-ring isolation.

The illustrated bores 320 are shown at normal incidence. Advantageously, applicant has found that with the degree of acoustic isolation provided by this O-ring mounting, sufficiently well-defined signals are obtained to take flow measurements in fluids such as gases in various ducts or conduits that are known in the trade as vents, pipes, headers and stacks, by using transducers spaced apart at a distance L appreciably smaller than the stack or conduit diameter, and mounted at normal or near-normal incidence on a plug or cap. For example, using a small reflector R in the stack or conduit as shown in FIG. 15A a downstream transducer 310b may catch the reflected signal transmitted by an upstream transducer, 310a, both mounted at normal incidence in a single plug or corner plate of small dimension. In smaller conduits the transducers may be mounted in separate bores directly in the conduit wall, or in a single clamp-on mounting block positioned over a wall opening or over a thinned wall position, while remaining substantially isolated from each other. In preferred one-port installations, the measurement of flow averaged over an interrogation path out to the reflector and back, would very nearly equal the area averaged flow velocity in the conduit and would be relatively insensitive to Reynolds Number Re at least for fully developed turbulent flow profiles. The examples in FIG. 15A have this property.

Figure 15B:
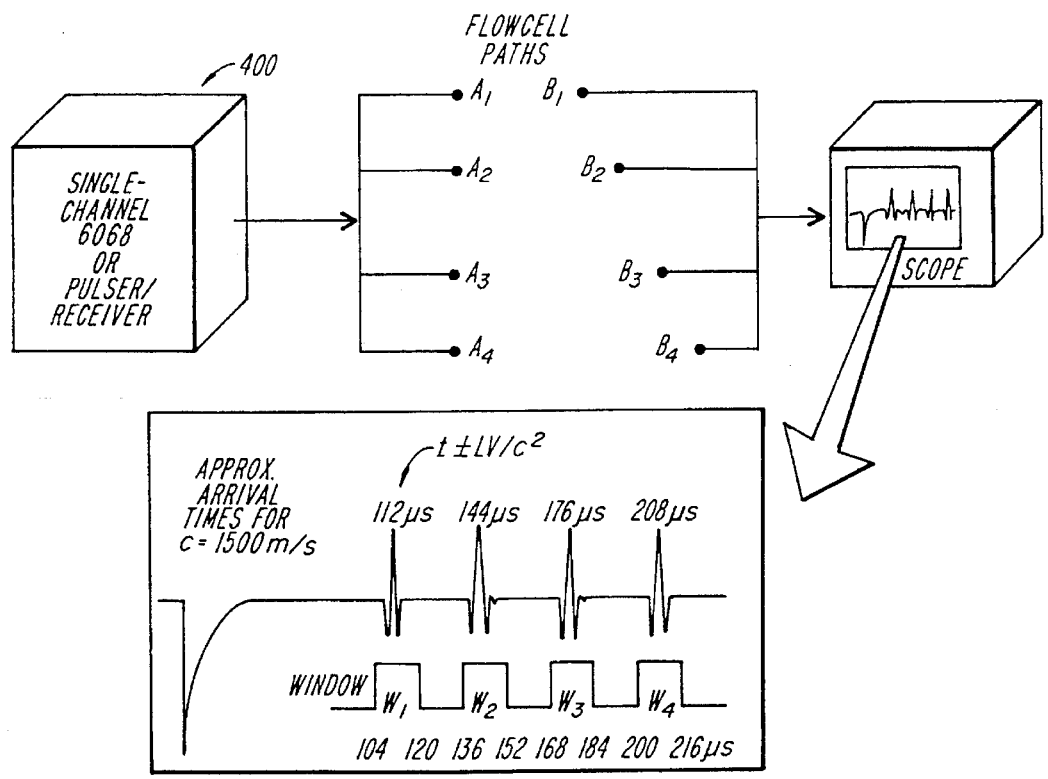

More complex arrangements of transducers in a single conduit, or with a single measurement instrument are thus possible. For example, as illustrated in FIG. 15B, each channel of a four-channel driver/intervalometer measuring instrument 400 such as a Panametrics Model No. GP68 may be attached, without switching, to each of the four sending and receiving transducers ($A_1$–$A_4$ and $B_1$–$B_4$) in four pipes, with the transducers in each pipe arranged to provide four different length paths with the transit time differences each greater than the ring-down time, so that the signals may be received in different time intervals in a single channel from each path of a given pipe with the transducers connected in parallel.

Figure 15C:
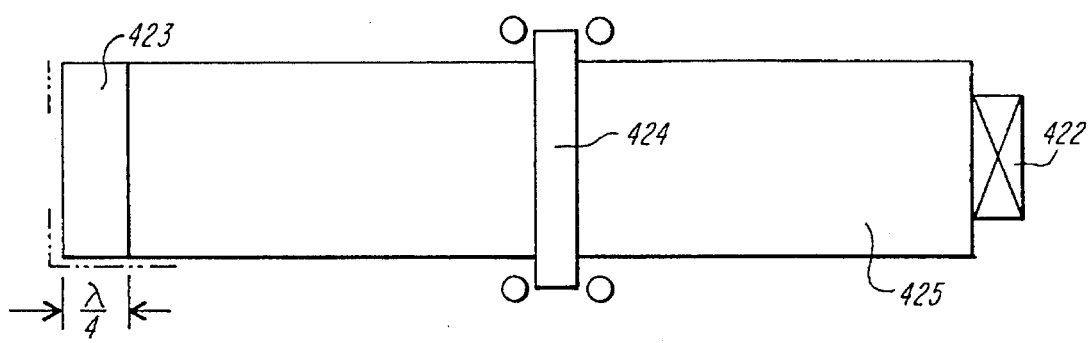

This O-ring isolation mounting is versatile, and in addition to use in a crystal housing or a rigidizing external frame as discussed above, may be applied to a buffer rod or standoff located between a transducer crystal and an impedance matching launching structure for gas interrogation. FIG. 15C shows such a configuration, wherein a transducer crystal 422 is coupled by a buffer rod 425 to a quarter wave coupling block 423, and a flange 424 located at approximately the rod's center of gravity is provided for isolation mounting between O-rings. This allows the crystal to be supported in relative thermal isolation as well as acoustic isolation, many wavelengths, and up to five or more pipe diameters, away from the conduit and fluid.

Figure 15D:
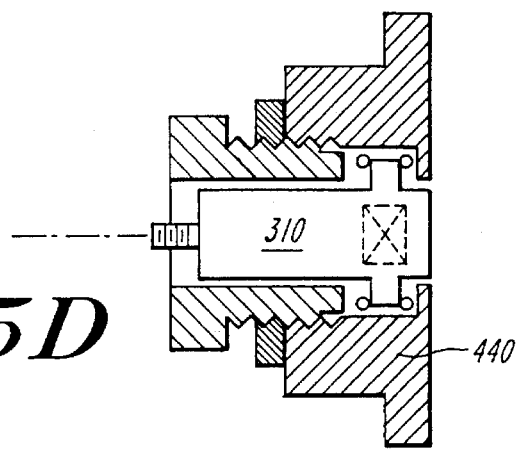
Figure 15E:
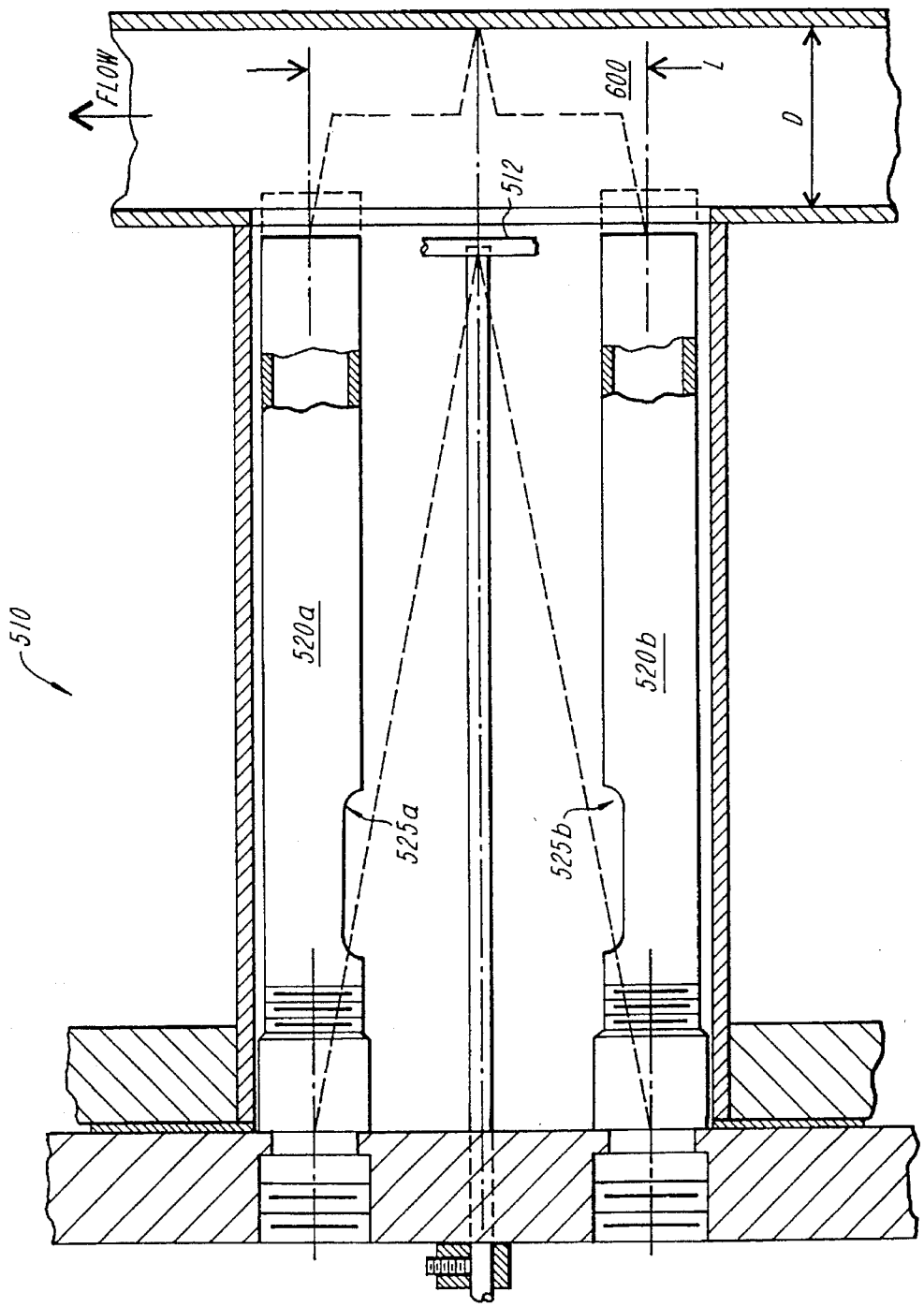
FIG. 15E illustrates a self-referencing one-port system using transducer isolation.

In FIG. 15E there is shown another one-port nozzle assembly 510, similar in some respects to that shown in FIG. 15A for interrogation perpendicular to a conduit, duct or stack. In FIG. 15E, however, there is a reference reflector 512 adjustably positioned very near the inside surface of the duct 600 in which flow is to be measured. This reflector provides a reference echo whose transit time provides a correction to transit times in the freestream across the duct, as is increasingly important if temperature gradients are present. The reference echo amplitude is proportional to the gas acoustic impedance, as mentioned elsewhere herein, and so can be processed to yield gas pressure or gas density. The amplitude of this echo in other circumstances can be used to monitor the cleanliness and integrity of the transducer system. FIG. 15E also shows two waveguiding tubes or pipes 520a, 520b, each concentric with the axis of its respective transducer, and extending essentially to the freestream. This construction avoids beamspread in the nozzle and also avoids most of the turbulence that might otherwise attenuate the signals before they even emerge from the nozzle into the freestream. The waveguiding tubes each have a slot 525a, 525b that allows a predetermined small fraction of the energy within each tube to leak intentionally along a vee path to the reference reflector and then be received in the other tube through a similar slot. The transducers, when installed in their respective transducer ports and operated at wavelengths just a small submultiple of the transducer aperture, e.g., 25, 50 or 100 kHz, approximately, for apertures about 15 to 30 mm, lead to sufficient beamspread to obtain the reference information using the vee path illustrated, and to also obtain flow information along the vee path shown in broken fashion in the duct itself. The schematic of the waveforms associated with this type of reference and freestream interrogations represents the important reference and flow echoes at A and B, in the simplified waveform sketch below the drawing.

Figure 16:
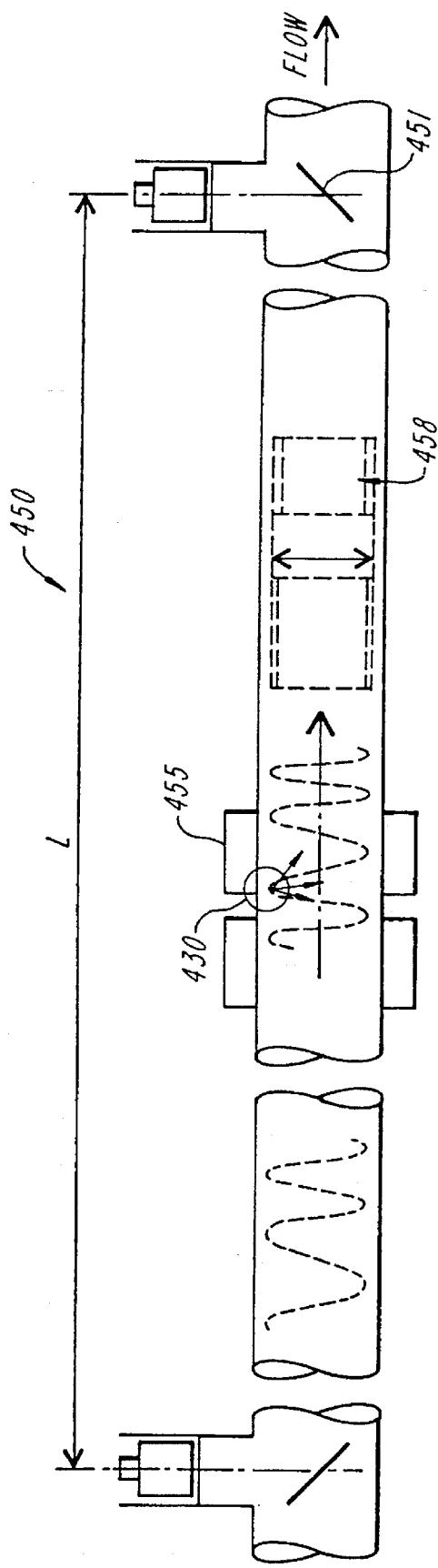
FIG. 16 illustrates signal isolation in a long, thin-walled flow cell of small diameter.

Returning now briefly to the first discussed isolation structure, that of alternating masses, a further embodiment with variations is shown in FIG. 16. This system 450 involves a measuring of length L with the signal path defined by reflector plates 451 to direct ultrasonic signals along the flow axis, with a plurality of massive collars 455 placed about the conduit, and/or thick sleeves 458 placed within the conduit. The sleeves may be of differing thickness, hence inner diameter, in order to better break up reflections from the interior of the duct. A spiral coil 430, which may be of constant, progressive or irregular pitch scatters in the conduit wall any energy reflected against the wall from the fluid, so that an essentially purely axial wave propagates in the fluid. This arrangement effectively filters or sharpens the signal trace by eliminating higher modes and spurious multi-path vibrations traveling with the ultrasonic signal but not propagating axially.

While the above descriptions have focused on the isolation achieved between the ends of a vessel or conduit on the one hand, or a transducer and its surrounding vessel or conduit on the other hand, the described isolation structures may also be applied to free-standing, externally-attached or unconfined transducers and measurement systems. In that case, a simple counterbored yoke or bracket 440 as shown in FIG. 15D may be mounted on a frame, rod, or existing structure such as a beam or culvert, to direct its signals into, or receive signals from, surrounding air.

Figure 17:
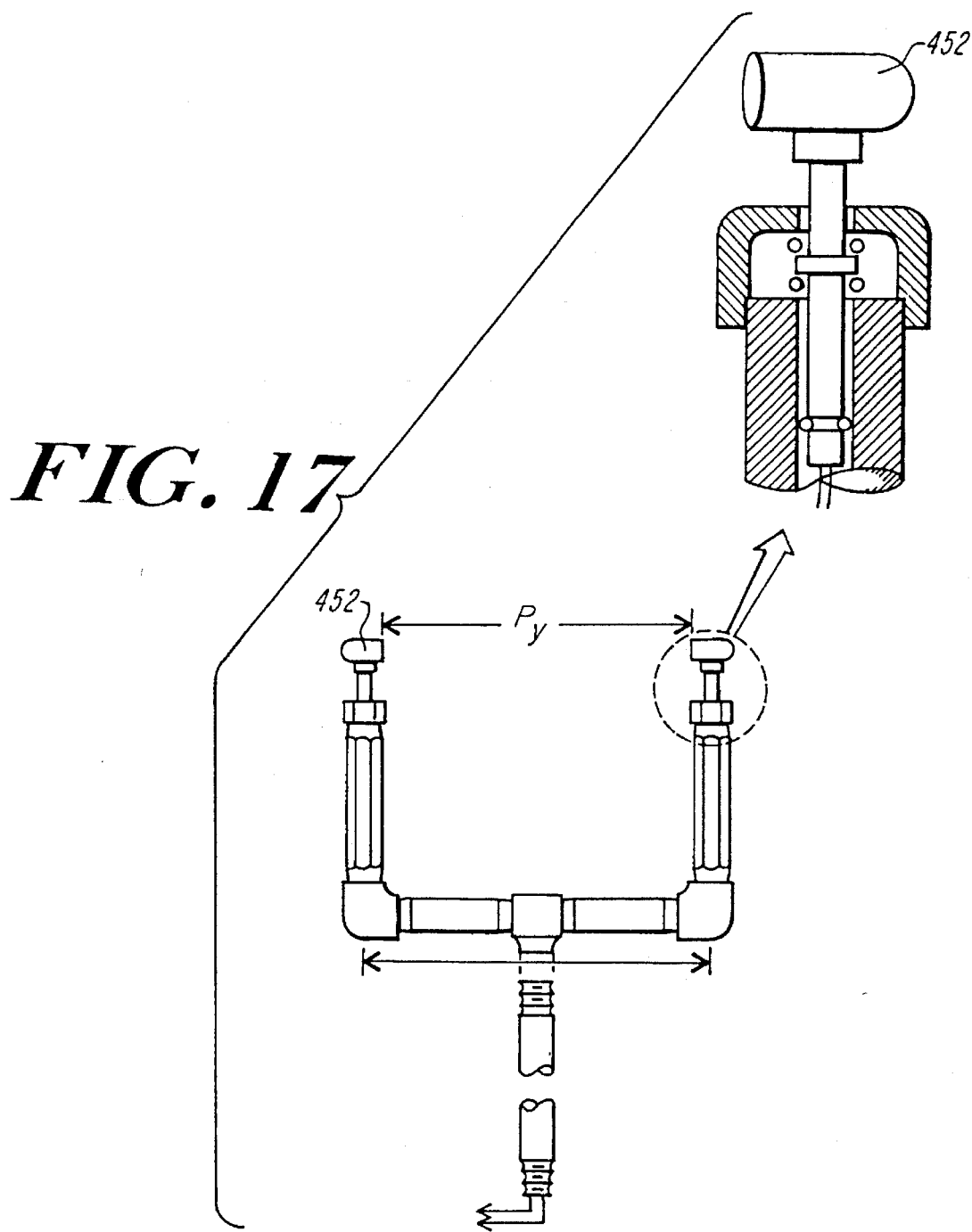
FIG. 17 illustrates the transducers of FIG. 15–15D in an unconfined measurement system.

One particularly elegant application of such point-like gas-exciting transducers is an ultrasonic anemometer 450, shown in FIG. 17. Three acoustically isolated transducers 451, 452, 453 are held by a rigid, non-rotating frame 456 having a body which directs the transducers along three independent pathways a, b, c having x, y, and z components, to receiving transducers 451,452, 453 positioned to sense the signal from its sending transducer, providing a readily derived contra-propagation transit time interval, or other measurement, from which wind direction or speed components are calculated. O-ring isolators are shown in the detailed view FIG. 17 of one pair of transducers.

Figure 18:
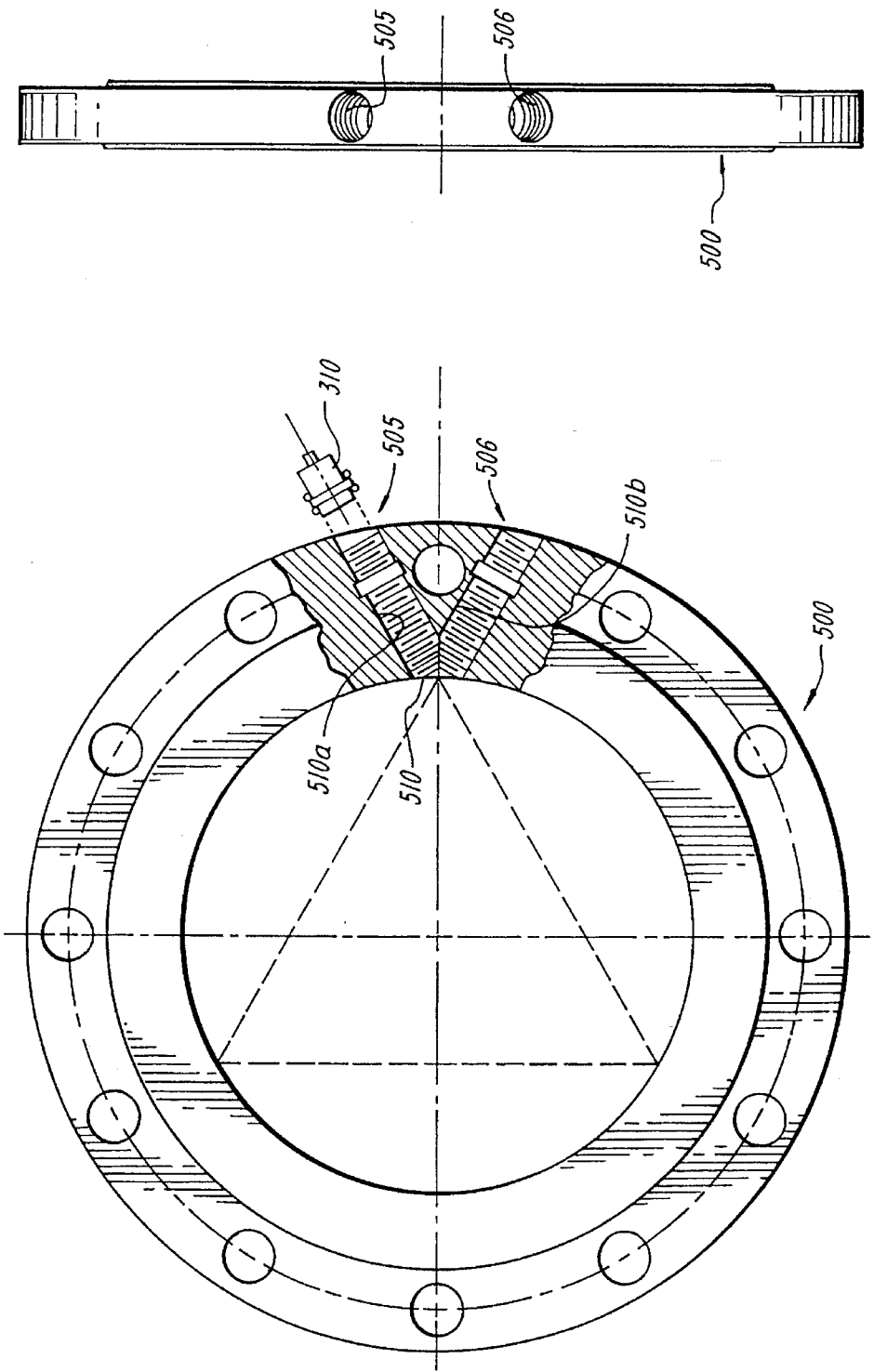

One particular application of this gas transducer signal technology is the provision of closed path signal loops, with the path defined by one or more transducers and/or reflectors, to measure a physical quantity corresponding to a path integral of interest. FIGS. 18 and 18A show a face view and an edge view, respectively, of a pipe flange 500 incorporating isolated transducers such as the transducers 310 of FIG. 15D.

A pair of transducer mounting bores 505,506 are formed in the flange 500 directed at angles to cross at a single opening 510 in the inner circumferential edge of the annular flange, which is illustratively sized to be clamped or bolted as a measurement collar in a ten inch steel pipe, with an opening or thinned wall formed in the pipe and aligned below the opening 510. The transducer path is aimed along a midradius path, tangent to an axially centered cylinder of radius one-half the pipe radius, so that the ultrasonic beam is reflected twice from the inner wall of the conduit, forming an inscribed equilateral triangle path between sending transducer 505 and receiving transducer 506. The signal path transit time, together with the known geometry of the flange, thus provides a closed loop path integral of signal velocity Vds on a three-leg path surrounding the pipe axis. This provides a direct measure of the circulation $\Gamma_z$ about the conduit axis. The two transducers are located adjacent each other in the solid flange. In the illustrated 10-inch flange, the circulation path is $L_c$=15×1.732 inches and the total gas path is approximately P=L+3.26 inches. To prevent gas-borne crosstalk in an arrangement where the two ports join as one, one must use a sufficiently high ultrasonic frequency, or modify the ports from the idealized geometry presented for illustrative purposes so that scatter from the "first" angled port does not get up into the "second" port by way of their common passageway.

Figure 19:
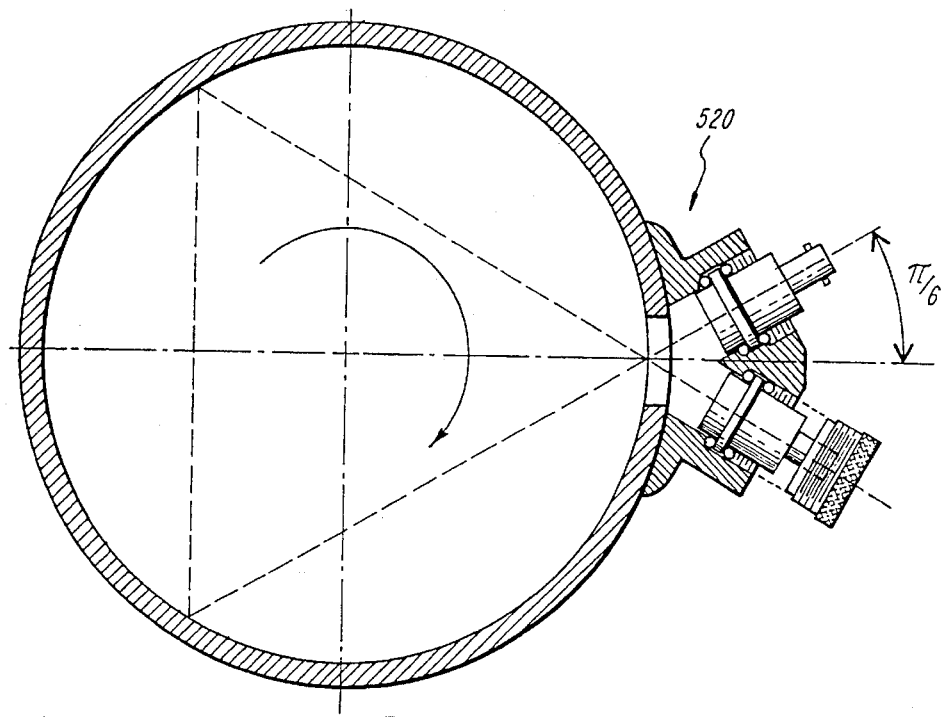
FIG. 19 illustrates another embodiment of a triple midradius circulation sensor.

FIG. 19 shows another embodiment of a device 520 for taking a midradius path measurement of circulation about the pipe axis. In this embodiment, a pair of isolated and angled transducers are mounted in an external block, directed along midchordal paths through a pipe opening. By alternating propagation along clockwise and counterclockwise paths a measure of the magnitude of swirl or circulation $\Gamma_z$ about the axis is obtained.

In other applications, isolation transducers may be mounted with separate reflector elements or opposed transducers to define different closed paths, or approximately planar closed paths for determining particular characteristics or deriving other components of fluid circulation.

Figure 20:
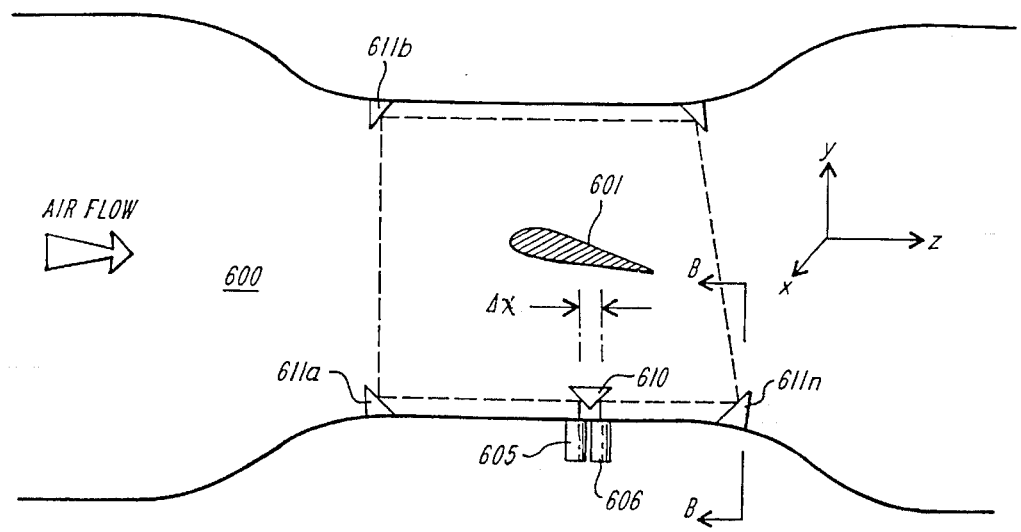

FIG. 20 shows another closed path sensor configuration 600, illustratively for sensing circulation $\Gamma_x$ about a test object 601 located in a wind tunnel. A pair of transducers 605,606 are directed at a beam splitting reflector 610 (or a pair of single beam reflectors) that, together with reflectors 611a, 611b, . . . 611n form a closed polygonal acoustic path around the object 601 between the two transducers. The transducer separation is selected to be small compared to the dimensions of the tunnel and the test object, so that the path is effectively a closed path. In lieu of the reflectors, separate transducers may define the endpoints of each segment, in which case more signal processing is required. The reflectors preferably are not located too close to the walls, in order to avoid inaccuracy that might arise due to gradients in the boundary layer.

As shown in FIG. 20A, a pair of reflectors located in adjacent planes may be used instead of beam splitter 610 to define a full contour around the test object ($\Delta z$=0). FIG. 20B is an end view, showing the vaned nature of the reflectors, which define measurement paths in closely adjacent planes while allowing normal airflow along the wind tunnel axis in the plane of interest.

In another embodiment shown in FIG. 21, by employing a spherical or cylindrical test chamber 550 which is smoothly enlarged from the nominal tunnel inlet and outlet, a single opening 555 (shown in detail in FIG. 21A) allows a triple midradius interrogation path using the chamber wall as a signal reflector. This provides a small number of paths, which are well centered in the air stream and require no protruding reflectors. As shown in FIG. 21A, the chamber opening may have a screen or mesh 556 along the interior wall contour to preserve smooth aerodynamic flow properties.

FIG. 22 illustrates in schema possible path integral measurements performed in this way. The circulation $\Gamma_x$ about a model extending in the x direction may be pieced together from path measurements made in parallel but slightly offset planes. For example, under reasonable assumptions of continuity, the integration path ABCD may be approximated with the segments A"B" and C"D" from one plane, and B'C' and D'A' from an adjacent plane, with both the " and ' planes located adjacent to the plane of interest. This minimizes the aerodynamic effects of the transducers or reflectors on flow in the plane of interest.

Similar polygonal paths may be set up ahead of the test object to determine the swirl velocity at the inlet, and the circulation $\Gamma_z$ about the z axis. Thus, all functions necessary to compute lift may be directly measured by ultrasonic signal interrogation and simple signal processing. Since lift=$\rho V_z \Gamma_x$, and (a) the amplitude of the received signal yields the gas density $\rho$; (b) conventional contrapropagation measurements yield $V_z$; and (c) clockwise and counterclockwise path measurements yield $\Gamma_x$, the product of these three quantities yields the sought lift.

Referring still to FIG. 22, it will be understood that in order to utilize the primed and double primed planes that are close enough in proximity that measurements in these planes closely approximate the closed path integral required for a circulation measurement, one must be able to isolate closely spaced transducers such as those at A' and A", B' and B", etc.

An alternate approximation to the closed path integral can also be obtained using a corner transducer assembly as shown in FIG. 22A. In this design, a pair of transducers 310 are sealed and held in place with their axes both in one plane, using the O-ring flange sandwich method. The housing 319 for the two transducers is itself secured inside a wind tunnel, typically at four places in the yz plane to measure circulation about the x axis, that is, about a model oriented along the x axis. Each transducer is held as in FIG. 15.

Figure 22B:
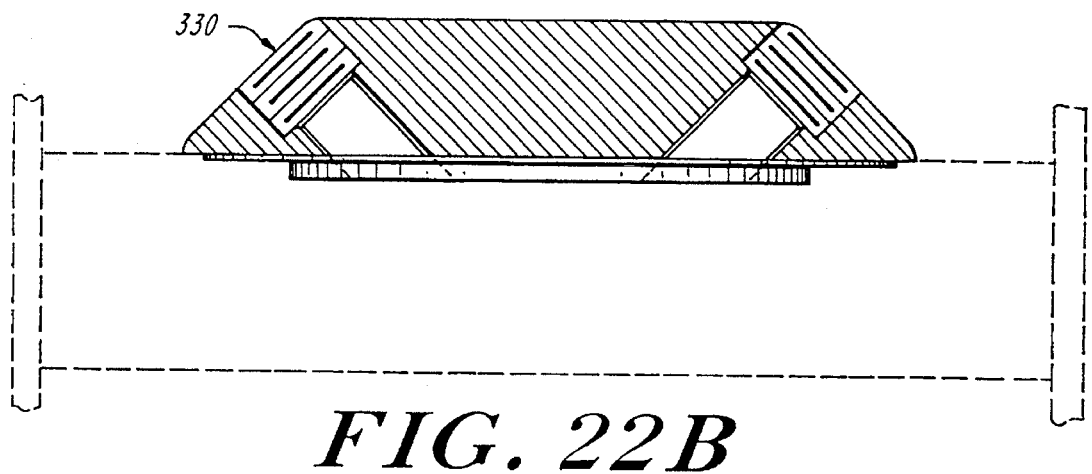

The ability to isolate by the O-ring flange sandwich method, two closely spaced transducers is also utilized in the blocklike housing 330 of FIG. 22B. This block is designed to be welded or otherwise sealably secured to a standard pipe.

The advantage of this block over prior art constructions is that the spacing of the transducers can be controlled more precisely than if one mounts separate angled coupling or nozzles onto the pipe. Previously, the separate blocks were often selected as the standard design approach, in order to achieve isolation.

As one reduces the frequency f at which the flow or other gas characteristic is measured, there is generally more beam spread and a greater tendency for signals to propagate over spurious (unwanted) gas paths. The remedies for this problem include judicious use of scatterers on surfaces from which no reflection is wanted. The use of a spiral or inserted sleeve was mentioned earlier. Other remedies include anechoically roughening or corrugating portions of the offending surface, or threading the surface if it is cylindrical and conveniently threaded by tapping or inserting a "threadsert," which is a form of spiraled insert normally used to secure screws.

Figure 22C:
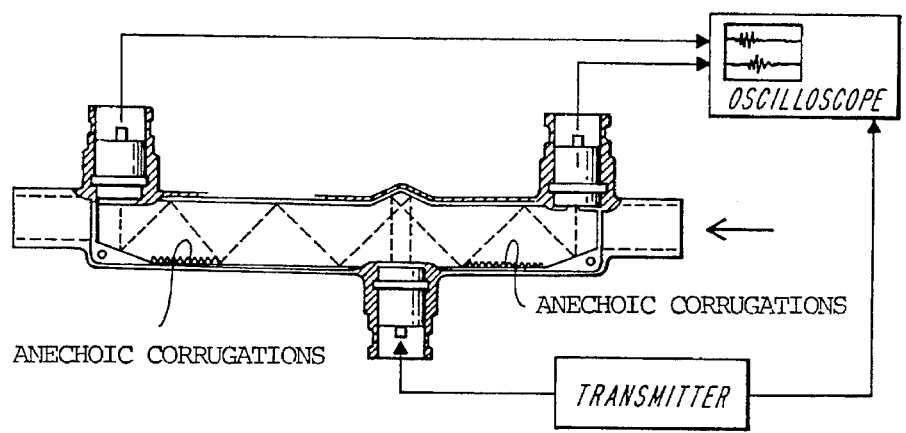

In the plastic square- or rectangularly channeled flowcell of FIG. 22C, the plastic wall is periodically corrugated, as shown; so too is the cover plate (not shown). The two cell sections connected in series illustrates a configuration for switchless fast response flow metering.

This completes a description of the principles of the invention, together with illustrative embodiments and several preferred constructions for diverse transducer isolation and gas or other fluid sensing applications. The invention being thus disclosed, variations and modifications thereof will occur to those skilled in the art, and such variations and modifications are included within the scope of the invention to which an exclusive right is asserted, as defined by the claims appended hereto.

What is claimed is:

1. A measurement system of the type wherein a transducer element is positioned in operative relation to a fluid medium to transduce mechanical wave energy in the medium, and having an isolation mounting for isolating the ultrasonic transducer element from surrounding elements of the measurement system to remove solid body noise transmission along paths outside the fluid medium, such isolation mounting comprising a flange and at least one O-ring of attenuating material supporting the flange and interrupting acoustic contact to the transducer.

2. A measurement system of the type wherein a transducer element is positioned in operative relation to a fluid medium to transduce mechanical wave energy in the medium, and having an isolation mounting for isolating the ultrasonic transducer element from surrounding elements of the measurement system to remove solid body noise transmission along paths outside the medium, such isolation mounting comprising a flange and a pair of O-rings of attenuating material supporting and forming a sandwich with said flange to interrupt acoustic contact.

3. A measurement system of the type wherein a transducer element is positioned in operative relation to a fluid medium to transduce mechanical wave energy in the medium, and having an isolation mounting for isolating the ultrasonic transducer element from surrounding elements of the measurement system to prevent solid body noise transmission along paths outside the fluid medium, such isolation mounting comprising a flange and at least one O-ring of attenuation material bearing against the flange to interrupt acoustic contact, wherein the flange is a flange of a conduit.

4. A measurement system according to claim 3, wherein the O-ring seats against an axially-directed face of the conduit.

5. A measurement system according to claim 3, wherein the O-ring seats in a chordally-directed bore in said flange.

6. A measurement system according to claim 1, wherein said flange is a flange of a cylindrical casing that houses said ultrasonic transducer element.

7. A measurement system according to claim 1, wherein said O-ring forms a primary seal for containing fluid in a container and said O-ring is compressed under 40% of its thickness.

8. A measurement system according to claim 1, wherein said O-ring forms a secondary seal for containing fluid in a container.

9. An isolation structure for interposing in a solid acoustic path between ultrasonic elements transmitting and receiving signals through a gas to attenuate noise transmitted along said solid path, and comprising a plurality of high impedance and low impedance segments arranged in series along the path, said segments being formed of elastic material and said low impedance segments having a thickness $<<\lambda/10$, where $\lambda$ is the wavelength of said signals in the solid acoustic path.

10. A measurement system according to claim 1, comprising housing means defining a flow channel for said medium, and a plurality of closely spaced ultrasonic transducer elements mounted in the housing means and directed along a measurement path, and having means for isolating at least one of said transducer elements from the housing means.

11. A measurement system according to claim 10, wherein the system comprises two transducer elements which transmit and receive signals along a single path, including three chordal segments to measure circulation about a flow axis.

12. A measurement system according to claim 10, wherein the system comprises at least two transducer elements that transmit and receive signals along a set of at least three segments, the set of segments together forming a closed contour lying substantially in a plane.

13. A measurement system according to claim 12, wherein the flow channel has an enlarged region with a substantially circular cross-section, and said closed contour is comprised of mid-radius chordal segments of said cross-section to measure circulation.

14. A measurement system according to claim 1, comprising a flow cell having a conduit for containing a fluid along a measurement path, the conduit having a thin wall effective to provide a phase velocity of acoustic signals propagated therethrough which is substantially less than velocity of said signals in a fluid in said conduit, and a frame for rigidly fixing measurement ends of the conduit, said frame including means for acoustically decoupling the frame between said ends.

15. A measurement system according to claim 1 wherein the fluid medium is a gas and said mechanical wave energy is ultrasonic wave energy which propagates for measurement of said ultrasonic wave energy in the gas, such system comprising a thin-walled conduit for containing said medium means for scattering in said thin-walled conduit energy of ultrasonic waves in said gas reflected from the conduit and a plurality of masses spaced apart from each other and each contacting the conduit wall along its length.

16. A measurement system according to claim 1, comprising wall means defining a fluid flow chamber a first plurality of ultrasonic transducer elements being acoustically isolated from said wall means and defining a first at least approximately planar closed signal path lying at least approximately in a first plane a second plurality of ultrasonic transducer elements being acoustically isolated from said wall means and defining a second at least approximately planar closed signal path lying at least approximately in a second plane.

17. A measurement system according to claim 16, wherein said second plane is positioned to be one of (i) a plane orthogonal to said first plane, and (ii) a plane adjacent and parallel to said first plane.

18. A measurement system according to claim 17, further comprising reflectors that define at least part of at least one of said first and second signal paths.

19. A measurement system according to claim 18, wherein one of said reflections lies in both said first and said second system paths.

* * * * *

UNITED STATES PATENT AND TRADEMARK OFFICE
CERTIFICATE OF CORRECTION

PATENT NO. : 5,515,733
DATED : May 14, 1996
INVENTOR(S) : Lawrence C. Lynnworth

It is certified that error appears in the above-identified patent and that said Letters Patent is hereby corrected as shown below:

Column 1, line 40, please replace "Snap-0n" with --Snap-On--;

Column 6, line 51, before "and possibly" please insert --costs--;

Column 11, line 25, please replace "192bcan" with --192b can--;

Column 12, line 7, please replace "µ/10" with --$\lambda$/10-- and "µ/2" with --$\lambda$/2--;

and

Column 12, line 25, please replace "50bis" with --50b is--.

Signed and Sealed this

Thirty-first Day of March, 1998

Attest:

BRUCE LEHMAN

*Attesting Officer*      *Commissioner of Patents and Trademarks*